United States Patent
Lorrain et al.

(10) Patent No.: US 10,925,872 B2
(45) Date of Patent: Feb. 23, 2021

(54) METHODS OF TREATING COCHLEAR SYNAPTOPATHY

(71) Applicant: PIPELINE THERAPEUTICS, INC., San Diego, CA (US)

(72) Inventors: Daniel Scott Lorrain, San Diego, CA (US); Michael Ming-Yuan Poon, San Diego, CA (US); Karin Joy Stebbins, San Clemente, CA (US)

(73) Assignee: Pipeline Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/470,182

(22) PCT Filed: Dec. 12, 2017

(86) PCT No.: PCT/US2017/065892
§ 371 (c)(1),
(2) Date: Jun. 14, 2019

(87) PCT Pub. No.: WO2018/111926
PCT Pub. Date: Jun. 21, 2018

(65) Prior Publication Data
US 2019/0307746 A1 Oct. 10, 2019

Related U.S. Application Data

(60) Provisional application No. 62/435,629, filed on Dec. 16, 2016, provisional application No. 62/515,839, filed on Jun. 6, 2017.

(51) Int. Cl.
| | | |
|---|---|---|
| *A61K 31/4985* | (2006.01) | |
| *A61K 9/00* | (2006.01) | |
| *A61K 9/08* | (2006.01) | |
| *A61K 31/427* | (2006.01) | |
| *A61K 31/5517* | (2006.01) | |
| *A61K 47/10* | (2017.01) | |
| *A61K 47/26* | (2006.01) | |
| *A61K 47/32* | (2006.01) | |
| *A61K 47/38* | (2006.01) | |
| *A61K 45/06* | (2006.01) | |
| *A61K 47/36* | (2006.01) | |
| *A61K 31/55* | (2006.01) | |
| *A61P 27/16* | (2006.01) | |

(52) U.S. Cl.
CPC ........ *A61K 31/4985* (2013.01); *A61K 9/0046* (2013.01); *A61K 9/08* (2013.01); *A61K 31/427* (2013.01); *A61K 31/55* (2013.01); *A61K 31/5517* (2013.01); *A61K 45/06* (2013.01); *A61K 47/10* (2013.01); *A61K 47/26* (2013.01); *A61K 47/32* (2013.01); *A61K 47/36* (2013.01); *A61K 47/38* (2013.01); *A61P 27/16* (2018.01)

(58) Field of Classification Search
CPC ................................................ A61K 31/4985
USPC ........................................................ 514/216
See application file for complete search history.

(56) References Cited

U.S. PATENT DOCUMENTS

| | | | |
|---|---|---|---|
| 6,890,956 | B2 | 5/2005 | Churcher et al. |
| 6,984,626 | B2 | 1/2006 | Nadin et al. |
| 7,049,296 | B2 | 5/2006 | Castro Pineiro et al. |
| 7,101,895 | B2 | 9/2006 | Churcher et al. |
| 7,138,400 | B2 | 11/2006 | Collins et al. |
| 7,144,910 | B2 | 12/2006 | Madin et al. |
| 7,160,875 | B2 | 1/2007 | Flohr et al. |
| 7,166,587 | B2 | 1/2007 | Flohr et al. |
| 7,183,303 | B2 | 2/2007 | Castro Pineiro et al. |
| 7,244,739 | B2 | 7/2007 | Cheng et al. |
| 7,253,158 | B2 | 8/2007 | Galley et al. |
| 8,084,477 | B2 | 12/2011 | Starrett, Jr. et al. |
| 8,188,069 | B2 | 5/2012 | Miller et al. |
| 2004/0029862 | A1 | 2/2004 | Belanger et al. |
| 2004/0049038 | A1 | 3/2004 | Collins et al. |
| 2004/0186147 | A1 | 9/2004 | Hannam et al. |
| 2005/0119293 | A1 | 6/2005 | Collins et al. |
| 2005/0143369 | A1 | 6/2005 | Castro Pineiro et al. |
| 2005/0182109 | A1 | 8/2005 | Collins et al. |
| 2005/0182111 | A1 | 8/2005 | Pineiro et al. |
| 2005/0215602 | A1 | 9/2005 | Campbell et al. |
| 2011/0020232 | A1 | 1/2011 | Eberhart et al. |
| 2011/0305674 | A1 | 12/2011 | Edge |
| 2012/0289558 | A1 | 11/2012 | Kounnas |
| 2015/0209367 | A1 | 7/2015 | Edge |
| 2015/0209406 | A1 | 7/2015 | Chen |
| 2015/0274721 | A1 | 10/2015 | Pettersson et al. |
| 2019/0194140 | A1 * | 6/2019 | Seiders .................. A61K 47/34 |

FOREIGN PATENT DOCUMENTS

| | | |
|---|---|---|
| WO | WO-98/28268 A2 | 7/1998 |
| WO | WO-98/28268 A3 | 7/1998 |
| WO | WO-01/70677 A1 | 9/2001 |
| WO | WO-02/49038 A1 | 6/2002 |

(Continued)

OTHER PUBLICATIONS

Fernandez et al., The. J. Neurosc. (2015) vpl. 35(19), pp. 7509-7520.*

Ruolun Qiu et al., Anovelgam masecretasemodulator: safety, tolerability, pharmacokinetics, and effects on plasma amyloid-b levels following single oral ascending doses in healthy volunteers, Poster Presentations, Alzheimer's & Dementia: The Journal of the Alzheimer's Association, Jul. 20, 2016, vol. 12 , No. 7, p. 61 I-p. 6 12, Poster No. PF-06648671 (DOI https://doi.org/ 10 .1 016 /j. jalz.2016.06.12 13).

(Continued)

*Primary Examiner* — Taofiq A Solola
(74) *Attorney, Agent, or Firm* — Anson M. Nomura; Mintz, Levin, Cohn, Ferris, Glovsky and Popeo, P.C.

(57) ABSTRACT

The present application describes the use of gamma secretase inhibitors and gamma secretase modulators for the treatment of cochlear synaptopathy.

28 Claims, 17 Drawing Sheets

(56) References Cited

FOREIGN PATENT DOCUMENTS

| WO | WO-03/093251 A1 | 11/2003 |
|---|---|---|
| WO | WO-03/093252 A1 | 11/2003 |
| WO | WO-03/093253 A1 | 11/2003 |
| WO | WO-03/093264 A1 | 11/2003 |
| WO | WO-2004/039370 A1 | 5/2004 |
| WO | WO-2004/039800 A1 | 5/2004 |
| WO | WO-2005/014553 A1 | 2/2005 |
| WO | WO-2005/023772 A1 | 3/2005 |
| WO | WO-2005/030731 A1 | 4/2005 |
| WO | WO-2009/087130 A1 | 7/2009 |
| WO | WO-2012/116965 A1 | 9/2012 |
| WO | WO-2014/039781 A1 | 3/2014 |
| WO | WO-2014/045156 A1 | 3/2014 |
| WO | WO-2015/007058 A1 | 1/2015 |
| WO | WO-2016/201168 A1 | 12/2016 |
| WO | WO-2017/007702 A1 | 1/2017 |
| WO | WO-2017/075264 A1 | 5/2017 |
| WO | WO-2017/075264 A8 | 5/2017 |
| WO | WO-2017/120465 A1 | 7/2017 |
| WO | WO-2017/127619 A1 | 7/2017 |

OTHER PUBLICATIONS

Bai, G. et al. (Oct. 6, 2011). "Protease regulation: the Yin and Yang of neural development and disease," *Neuron* 72(1):9-21.
Bharadwaj, H.M. et al. (Feb. 21, 2014). "Cochlear neuropathy and the coding of supra-threshold sound," *Front Syst Neurosci* 8:26.
Bursavich, M.G. et al. (Aug. 25, 2016, e-published Apr. 5, 2016). "Gamma Secretase Modulators: New Alzheimer's Drugs on the Horizon?" *J Med Chem* 59(16):7389-7409.
Crump, C.J. et al. (May 14, 2013, e-published May 2, 2013). "Development and mechanism of γ-secretase modulators for Alzheimer disease," *Biochemistry* 52(19):3197-3216.
Defourny, J. et al. (2013). "Ephrin-A5/EphA4 signalling controls specific afferent targeting to cochlear hair cells," *Nat Commun* 4:1438.
Forcet, C. et al. (May 23, 2002). "Netrin-1-mediated axon outgrowth requires deleted in colorectal cancer-dependent MAPK activation," *Nature* 417(6887):443-447.
Haapasalo, A. et al. (2011). "The many substrates of presenilin/γ-secretase," *J Alzheimers Dis* 25(1):3-28.
Jeon, S.J. et al. (Jun. 8, 2011). "Notch signaling alters sensory or neuronal cell fate specification of inner ear stem cells," *J Neurosci* 31(23):8351-8358.
Kim, Y.J. et al. (Apr. 4, 2016). "Dcc Mediates Functional Assembly of Peripheral Auditory Circuits," *Sci Rep* 6:23799.
Kounnas, M.Z. et al. (Sep. 9, 2010). "Modulation of gamma-secretase reduces beta-amyloid deposition in a transgenic mouse model of Alzheimer's disease," *Neuron* 67(5):769-780.
Kounnas, M.Z. et al. (Jan. 2017). "NGP 555, a γ-Secretase Modulator, Lowers the Amyloid Biomarker, Aβ 42, in Cerebrospinal Fluid while Preventing Alzheimer's Disease Cognitive Decline in Rodents," *Alzheimer's & Dementia: Translational Research & Clinical Interventions* 3(1):65-73.
Kujawa, S.G. et al. (Nov. 11, 2009). "Adding insult to injury: cochlear nerve degeneration after "temporary" noise-induced hearing loss," *J Neurosci* 29(45):14077-14085.
Lee, K.H. et al. (Feb. 2008). "Promotion of neurite outgrowth and axon guidance in spiral ganglion cells by netrin-1," *Arch Otolaryngol Head Neck Surg* 134(2):146-151.
Liberman, M.C. et al. (Sep. 12, 2016). "Toward a Differential Diagnosis of Hidden Hearing Loss in Humans," *PLOS One* 15 pages.
Lin, H.W. et al. (Oct. 2011, e-published Jun. 18, 2011). Primary neural degeneration in the Guinea pig cochlea after reversible noise-induced threshold shift, *J Assoc Res Otolaryngol* 12(5):605-616.
Ma, E.Y. et al. (Feb. 27, 2008). "Notch signaling regulates the extent of hair cell regeneration in the zebrafish lateral line," *J Neurosci* 28(9):2261-2273.
Mizutari, K. et al. (Jan. 9, 2013). "Notch inhibition induces cochlear hair cell regeneration and recovery of hearing after acoustic trauma," *Neuron* 77(1):58-69.
Omata, Y. et al. (Mar. 2016). "Expression of amyloid-β in mouse cochlear hair cells causes an early-onset auditory defect in high-frequency sound perception," *Aging* 8(3):427-439.
Parent, A.T. et al. (Feb. 9, 2005). "Presenilin attenuates receptor-mediated signaling and synaptic function," *J Neurosci* 25(6):1540-1549.
Schaette, R. et al. (Sep. 21, 2011). "Tinnitus with a normal audiogram: physiological evidence for hidden hearing loss and computational model," *J Neurosci* 31(38):13452-13457.
Suzuki, J. et al. (Apr. 25, 2016). "Round-window delivery of neurotrophin 3 regenerates cochlear synapses after acoustic overexposure," *Sci Rep* 6:24907.
Taniguchi, Y. et al. (Aug. 15, 2003, e-published Jul. 2, 2003). "Presenilin-dependent "gamma-secretase" processing of deleted in colorectal cancer (DCC)," *J Biol Chem* 278(33):30425-30428.
Tona, Y. et al. (May 22, 2014). "Therapeutic potential of a gamma-secretase inhibitor for hearing restoration in a guinea pig model with noise-induced hearing loss," *BMC Neurosci* 15:66.
Valero, M.D. et al. (Sep. 2017, e-published Jul. 8, 2017). "Noise-induced cochlear synaptopathy in rhesus monkeys (*Macaca mulatta*)," *Hear Res* 353:213-223.
Wan, G. et al. (Nov. 2015, e-published Apr. 30, 2015). "No longer falling on deaf ears: mechanisms of degeneration and regeneration of cochlear ribbon synapses," *Hear Res* 329:1-10.
Yamamoto, N. et al. (Jan. 2006, e-published Nov. 8, 2005). "Inhibition of Notch/RBP-J signaling induces hair cell formation in neonate mouse cochleas," *J Mol Med* 84(1):37-45.
Zine, A. et al. (Jul. 1, 2001). "Hes1 and Hes5 activities are required for the normal development of the hair cells in the mammalian inner ear," *J Neurosci* 21(13):4712-4720.

\* cited by examiner

FIG. 1A
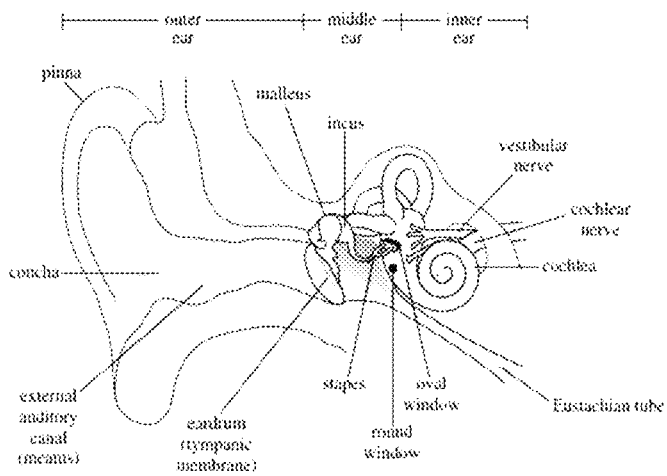
FIG. 1B
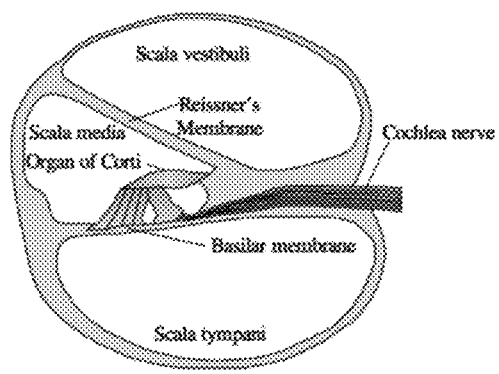
FIG. 1C
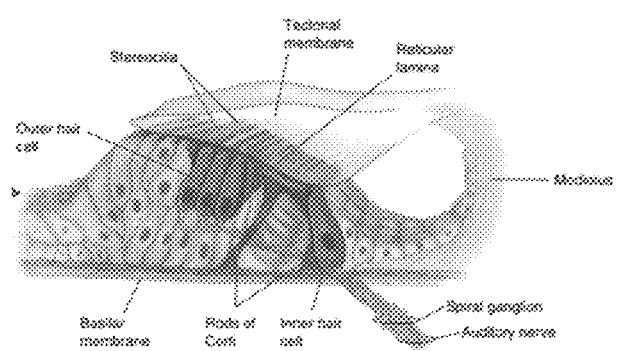
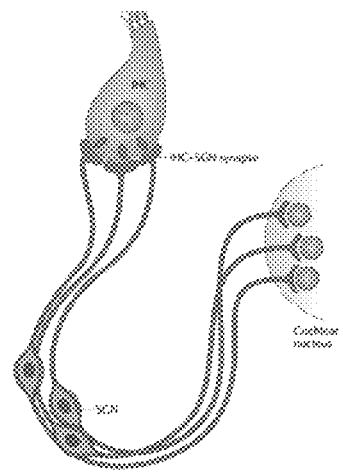
FIG. 1D

*1-way ANOVA, Tukey's post-hoc (compared to 98dB vehicle)*

| | |
|---|---|
| Compound I |  |
| Compound II |  |
| BMS-708163 |  |
| RO4929097 |  |
| Compound X |  |
| DAPT |  |

| | |
|---|---|
| L-685458 |  |
| BMS-299897 |  |
| MK-0752 |  |
| YO-01027 |  |
| LY411575 |  |
| ELN-46719 | 2-hydroxy-valeric acid amide analog of LY411575 |
| PF-03084014 |  |

| | |
|---|---|
| semagacestat |  |
| begacestat |  |
| MRK-003 |  |
| MRK-560 |  |
| JLK 6 |  |
| ALX-260-127 |  |

| | |
|---|---|
| "RO" |  |
| CHF5074 |  |
| EVP-0015962 |  |
| E2012 |  |
| E2212 |  |
| BMS-869780 |  |
| BMS-932481 |  |

| | |
|---|---|
| JNJ-40418677 |  |
| JNJ-42601572 |  |
| BIIB042 |  |
| SPI-1810 |  |
| NGP555 |  |
| PF06648671 |  |
| FRM-36143 |  |

METHODS OF TREATING COCHLEAR SYNAPTOPATHY

INCORPORATION BY REFERENCE TO RELATED APPLICATIONS

Any and all priority claims identified in the Application Data Sheet, or any correction thereto, are hereby incorporated by reference under 37 C.F.R. § 1.57. This application is U.S. National Phase under 35 U.S.C. § 371 of International Application No. PCT/US2017/065892, filed Dec. 12, 2017, designating the U.S. and published in English as International Pub. No. WO 2018/111926, which claims the benefit of U.S. Provisional Application No. 62/435,629, filed Dec. 16, 2016, and U.S. Provisional Application No. 62/515,839, filed Jun. 6, 2017. Each of the aforementioned applications is incorporated by reference herein in its entirety, and each is hereby expressly made a part of this specification.

BACKGROUND

Hearing Loss

Over 5% of the world's population suffers from some form of disabling hearing impairment (WHO Fact Sheet No. 300 "Deafness and Hearing Loss", updated March 2015). The majority of these cases result from sensorineural hearing loss (SNHL) which refers to an impairment resulting from damage or loss of function of the cochlea—and/or—auditory nerve. Most cases of SNHL present with a gradual deterioration of hearing thresholds occurring over years to decades. It may be accompanied by other symptoms such as ringing in the ears (tinnitus), dizziness or lightheadedness (vertigo). SNHL can be inherited or acquired (e.g. noise-induced). It may be congenital or develop later in life. The most common kind of sensorineural hearing loss is age-related (presbycusis), followed by noise-induced hearing loss (NIHL).

Direct damage to hair cells within the cochlea accounts for many cases of SNHL. Here, sound waves travel through the fluid filled compartment of the cochlea vibrate inner ear sensory hair cells. If the vibration is strong enough hair cells can become damaged and die. This is an irreversible process in mammals and can be easily identified by a shift in auditory brainstem response (ABR) threshold and reduction in distortion product otoacoustic emissions (DPOAE).

Recent work on age-related and noise-induced hearing loss shows that the synapses, and not hair cells, may be the most vulnerable components of the inner ear leading to hearing deficits (Kujawa S G and Liberman M C, *J Neurosci.* 2009, 29(45): 14077-14085). These specialized synapses form the bridge between spiral ganglion cells of the auditory nerve and inner ear sensory hair cells (Safieddine S, et al., *Annu Rev Neurosci.* 2012, 35: 509-528). Each spiral ganglion neuron (SGN) sends a single peripheral axon to the organ of corti, where it contacts a single inner hair cell (IHC) via a single unmyelinated terminal dendrite within the organ of corti (Liberman M C, *Hear Res.* 1980, 3(1): 45-63). Loss or damage to these synapses (termed cochlear synaptopathy or auditory synaptopathy) can lead to profound effects on hearing and represents an important form of sensorineural hearing loss. Cochlear synaptopathy is a likely contributor to a variety of auditory perceptual abnormalities common with aging and after noise exposure, including speech-in-noise difficulties (Bharadwaj H M, et al., *Front Syst Neurosci.* 2014, 8(26)), tinnitus and hyperacusis (Gu J W, et al., *J Neurophysiol.* 2010, 104(6): 3361-70; Schaette R and McAlpine M., *J Neurosci.* 2011, 31(38): 13452-57). Unlike damage to outer hair cells, subjects with loss or damage to the synapse may exhibit normal ABR thresholds and normal DPOAEs but sustained deficits in auditory brainstem (ABR) wave I amplitude (Kujawa S G and Liberman M C, *J Neurosci.* 2009, 29(45): 14077-14085; Lin H W, et al., *JARO* 2011, 12: 605-616). Subjects with cochlear synaptopathy exhibit normal audiograms (have the ability to detect sound at normal thresholds), but lack the ability to analyze suprathreshold sounds, that is, sounds across a large dynamic range of sound frequencies and intensities. Such sound processing is important in recognizing speech or other sound content above competing background noise. This type of hearing loss has been called "hidden hearing loss" (see, e.g., Wan G and Corfas G., *Hear Res.* 2015, 329: 1-10; Moser T and Starr A, *Nature Reviews Neurology,* 2016, 135-149) because less than dramatic synaptic and neural losses are not revealed by standard threshold based assessments.

Currently there are no approved pharmacological or biological treatments for individuals with cochlear synaptopathy; while modern hearing aids may help to manage this type of hearing deficit, many patients do not respond well to hearing aids. As synaptic connections do not recover spontaneously, novel pharmacological therapies aimed at restoring synaptic connections are needed. In a recent study, noise-exposed mice that received delivery of neurotrophin-3 (NT-3) to the round window niche recovered inner hair cell synapses and a corresponding improvement in ABR wave 1 amplitude (Suzuki J, et al., *Scientific Reports.* 2016. Doi: 10.1038/srep24907). This is not surprising as NT3 is a growth factor that binds to TrkC receptors and is well known for its effects on neuronal survival and synaptogenesis. The use of Trk agonists for treating cochlear synaptopathy is disclosed in WO2017120465, published Jul. 13, 2017.

Ear and Hearing

The ear is divided into three main parts: the external ear, the middle ear and the inner ear. The external ear consists of the pinna, the external auditory canal, and the outward facing portion of the tympanic membrane, also known as the ear drum. The function of the external ear, in part, is to gather and direct sound waves towards the tympanic membrane and the middle ear.

Behind the tympanic membrane lies the middle ear, an air-filled cavity containing three bones called the ossicles: the malleus, the incus and the stapes. The auditory ossicles are linked together via tiny ligaments to form a bridge across the space of the cavity, with the malleus attached to the tympanic membrane at one end, and at the other end the stapes attached to the oval window of the cochlea in the inner ear. Sound waves from the external ear first cause the tympanic membrane to vibrate. The vibration is transmitted through the auditory ossicles and the oval window to the cochlea, transferring motion to the fluids in the inner ear.

The fluid-filled inner ear consists of two major components: the cochlea and the vestibular apparatus. The vestibular apparatus is the organ of balance, whereas the cochlea is the portion involved in hearing. The cochlea is a tube-like structure which is coiled into a shape resembling a snail. The inside of the cochlea is divided into three regions defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. In between the scala vestibuli and the scala tympani is the scala media, which ends as a closed sac at the apex of the cochlea, and contains endolymph fluid having potassium as its principal ion.

The cochlea is also tonotopically organized, meaning that different frequencies of sound waves interact with different locations on the structure. Such frequency tuning within the inner ear is attributable in part to the geometry of the basilar membrane, which is wider and more flexible at the apical end and narrower and stiffer at the basal end. The points responding to high frequencies are at the base of the basilar membrane, and the points responding to low frequencies are at the apex, giving rise to a topographical mapping of frequency (that is, to tonotopy).

The organ of Corti, the sensory organ for hearing that allows for the transduction of sound vibrations into neural signals, is located on the basilar membrane and contains the auditory sensory cells known as hair cells. The two types of hair cells, inner hair cells (IHCs) and outer hair cells (OHCs), are arranged in one row of IHCs and three rows of OHCs within the organ of Corti. Sound wave transmitted to the inner ear creates a pressure wave to propagate in the fluids of the cochlea (traveling wave) causing the basilar membrane (and along with it, the organ of Corti) to vibrate up and down. The vibration pattern depends on the intensity and frequency of the incoming sound. The vibration of the basilar membrane is amplified by the OHCs allowing the perception of even very quiet sounds. The OHCs also fine tune the frequency resolution of the basilar membrane. The OHCs also produce sounds that can be detected in the external auditory meatus with sensitive microphones. These internally generated sounds, termed otoacoustic emissions, are now used to screen newborns for hearing loss. OHCs are very sensitive to insults and their damage results in the most common type of hearing loss—a moderate sensorineural hearing loss where soft sounds below conversational speech are inaudible—yet loud sounds are perceived as loud.

IHCs are the primary auditory sensory cells that relay information encoded by the vibration pattern in the cochlear to the auditory nerve by transforming mechanical signal to electrical neural signal. IHCs are innervated with afferent neurons that are a subpopulation (Type I) of spiral ganglion neurons (SGNs). "Inner hair cell afferent synapses" refers to synaptic connections between IHC and afferent nerve fibers of Type I SGN; each IHC can form upwards of 20 synaptic connections with Type I SGNs, whereas each Type I SGN forms connection with only one IHC. While loss of synapses occurs in normal aging ears, noise exposures also cause such losses leading eventually to time-delayed loss of SGNs and permanent hearing loss.

While recent animal studies suggest that local delivery of neutrophin-3 (NT-3) may be a potential treatment for cochlear synaptopathy, there is currently no accepted treatment for cochlear synaptopathy. There remains a need for novel pharmacological therapies to restore synaptic connections in the cochlea.

SUMMARY

The present application is directed, in part, to the surprising and unexpected discovery that gamma secretase inhibitors (GSIs) and gamma secretase modulators (GSMs) (collectively referred to as GSI/Ms) can regenerate IHC synapses in animals exposed to pathogenic noise levels. This suggests that GSI/Ms may be effective in treating conditions associated with IHC synapse loss, including, but not limited to conditions described as hidden hearing loss. The present application is also directed, in part, to the surprising and unexpected discovery that GSI/Ms cause neurite outgrowth in in vitro culture assays containing spiral ganglion cells. Accordingly, some embodiments of the present application relate to treating and/or ameliorating one or more conditions associate with loss of synapses, in particular the loss of cochlear synapses.

Some embodiments provide methods for treating cochlear synaptopathy in a patient in need thereof which comprises administering to said patient a therapeutically effective amount of a gamma secretase inhibitor, a gamma secretase modulator, or a pharmaceutically acceptable salt of any of the foregoing. In some embodiments, said cochlear synaptopathy is hidden hearing loss. In some embodiments, said cochlear synaptopathy is tinnitus.

Some embodiments provide methods for treating hearing loss resulting from loss of inner hair cell afferent synapses in a patient in need thereof which comprises administering to said patient a therapeutically effective amount of a gamma secretase inhibitor, a gamma secretase modulator, or a pharmaceutically acceptable salt of any of the foregoing.

Some embodiments provide methods for treating tinnitus resulting from loss of inner hair cell afferent synapses in a patient in need thereof which comprises administering to said patient a therapeutically effective amount of a gamma secretase inhibitor, a gamma secretase modulator, or a pharmaceutically acceptable salt of any of the foregoing.

Some embodiments provide methods for treating hearing loss in a patient in need thereof who exhibits normal ABR threshold and/or normal DPOAE comprising administering to said patient a therapeutically effective amount of a gamma secretase inhibitor, a gamma secretase modulator, or a pharmaceutically acceptable salt of any of the foregoing, wherein said patient shows no obvious deficit in ABR threshold and DPOAE.

In some embodiments, said patient exhibits decreased amplitude in ABR wave I potential compared to normal-hearing patients. In some embodiments, said patient exhibits ABR wave V latency shifts with increasing background noise. In some embodiments, said patient exhibits elevated SP/AP ratio (summating potential to action potential ratio) as determined by electrocochleography compared to normal-hearing patients. In some embodiments, said patients perform more poorly on word recognition performance tests compared to normal-hearing patients.

Some embodiments comprise administering a gamma secretase inhibitor or a pharmaceutically acceptable salt thereof.

Some embodiments comprise administering a gamma secretase modulator or a pharmaceutically acceptable salt thereof. In some embodiments, said gamma secretase modulator, or a pharmaceutically acceptable salt thereof, selected from the group consisting of:

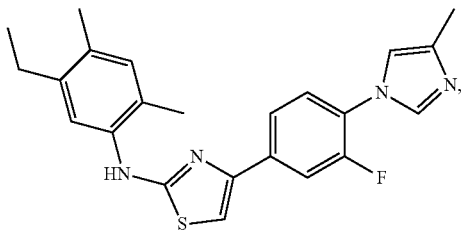

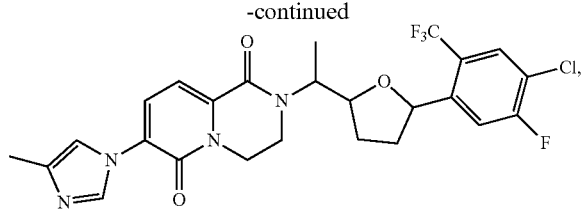

and pharmaceutically acceptable salts of any of the foregoing.

Some embodiments comprise administering a gamma secretase inhibitor or a pharmaceutically acceptable salt thereof. In some embodiments, said gamma secretase inhibitor, or a pharmaceutically acceptable salt thereof, is selected from the group consisting of: (2,2,3,3,3-pentafluoropropyl)-carbamic acid (S)-1-((S)-6-oxo-6,7-dihydro-5H-dibenzo[b,d]azepin-7-ylcarbamoyl) ethyl ester and (2R)-2-fluoro-2-methyl-N—[(S)-5-methyl-6-oxo-6,7-dihydro-5H-dibenzo[b,d]azepin-7-yl]-N'-(2,2,3,3,3- pentafluoropropyl)malonamide or a pharmaceutically acceptable salt of any of the foregoing.

In some embodiments, said gamma secretase inhibitor, gamma secretase modulator, or a pharmaceutically acceptable salt of any of the foregoing, is administered to or near the round window of the cochlea.

In some embodiments, said gamma secretase inhibitor, gamma secretase modulator, or a pharmaceutically acceptable salt of any of the foregoing, is administered via the oral route.

In some embodiments, said gamma secretase inhibitor, gamma secretase modulator, or a pharmaceutically acceptable salt of any of the foregoing, is administered intratympanically.

Some embodiments comprise administering a gamma secretase modulator.

In some embodiments, said gamma secretase modulator, or a pharmaceutically acceptable salt thereof, is selected from the group consisting of:

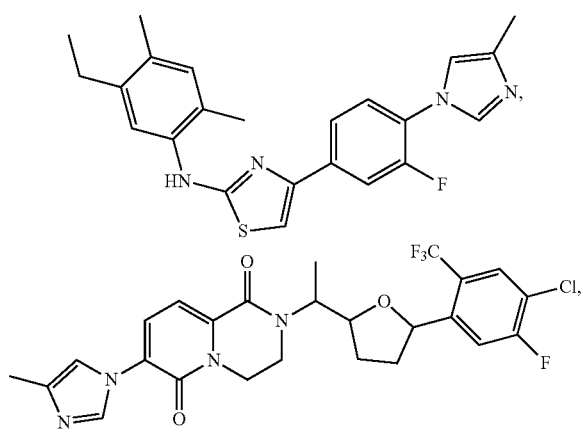

and pharmaceutically acceptable salts of any of the foregoing.

Some embodiments comprise administering a gamma secretase inhibitor. In some embodiments, said gamma secretase inhibitor, or a pharmaceutically acceptable salt thereof, is selected from the group consisting of: (2,2,3,3,3-pentafluoropropyl)-carbamic acid (S)-1-((S)-6-oxo-6,7-dihydro-5H-dibenzo[b,d]azepin-7-ylcarbamoyl) ethyl ester, (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, and pharmaceutically acceptable salts of any of the foregoing.

Some embodiments comprise administering a gamma secretase modulator. In some embodiments, said gamma secretase modulator, or a pharmaceutically acceptable salt thereof, is selected from the group consisting of:

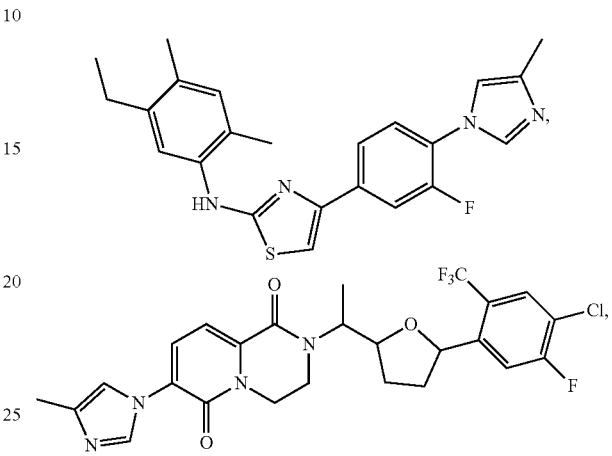

and pharmaceutically acceptable salts of any of the foregoing.

Some embodiments comprise administering a gamma secretase inhibitor, or a pharmaceutically acceptable salt thereof. In some embodiments, said gamma secretase inhibitor, or a pharmaceutically acceptable salt thereof, is selected from the group consisting of: (2,2,3,3,3-pentafluoropropyl)-carbamic acid (S)-1-((S)-6-oxo-6,7-dihydro-5H-dibenzo[b,d]azepin-7-ylcarbamoyl) ethyl ester, (2R)-2-fluoro-2-methyl-N—[(S)-5-methyl-6-oxo-6,7-dihydro-5H-dibenzo[b,d]azepin-7-yl]-N'-(2,2,3,3,3- pentafluoropropyl)malonamide, and pharmaceutically acceptable salts of any of the foregoing.

Some embodiments comprise administering a gamma secretase modulator. In some embodiments, said gamma secretase modulator selected from the group consisting of:

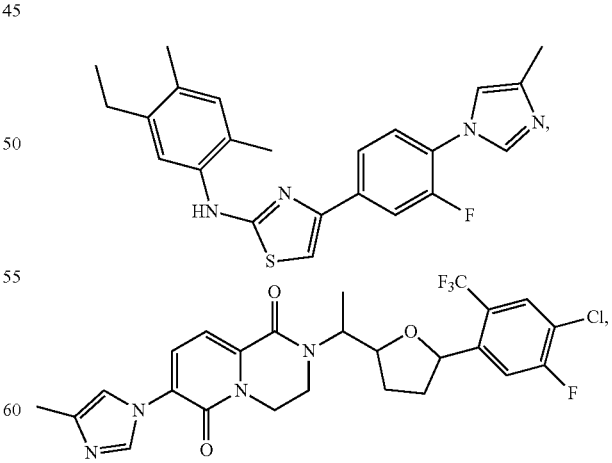

and pharmaceutically acceptable salts of any of the foregoing.

Some embodiments comprise administering a gamma secretase inhibitor, or a pharmaceutically acceptable salt thereof. In some embodiments, said gamma secretase inhibitor selected from the group consisting of: (2,2,3,3,3-pentafluoropropyl)-carbamic acid (S)-1-((S)-6-oxo-6,7-dihydro-5H-dibenzo[b,d]azepin-7-ylcarbamoyl) ethyl ester, (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, and pharmaceutically acceptable salts of any of the foregoing.

In some embodiments, said gamma secretase inhibitor, or a pharmaceutically acceptable salt thereof, is administered in a pharmaceutical composition comprising a pharmaceutically acceptable aqueous solution comprising:
(A) approximately 15% to 25% by weight (w/w) of poloxamer 407; or
(B) (i) approximately 15% to 25% by weight (w/w) of poloxamer 407 and (ii) approximately 0.5% to 4% by weight (w/w) of hydroxypropyl methylcellulose having a nominal viscosity of 40-60 cP or grade 80-120 cP; or
(C) (i) approximately 10%-20% by weight (w/w) of poloxamer 407, and (ii) approximately 0.1%-0.3% by weight (w/w) of Carbopol® 974P; or
(D) (i) approximately 0.5% to 8% by weight (w/w) of a hyaluronic acid; or
(E) (i) approximately 0.5% to 4% by weight (w/w) of a hyaluronic acid, and (ii) approximately 5% to 20% by volume of polyethylene glycol 400;
wherein said gamma secretase inhibitor is present in approximately 0.01% to about 20% w/v of said aqueous solution.

In some embodiments, said gamma secretase inhibitor is selected from crystalline (2,2,3,3,3-pentafluoropropyl)-carbamic acid (S)-1-((S)-6-oxo-6,7-dihydro-5H-dibenzo[b,d]azepin-7-ylcarbamoyl) ethyl ester, crystalline (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, and pharmaceutically acceptable salts of any of the foregoing.

In some embodiments, said pharmaceutically acceptable aqueous solution comprises approximately 15% to 25% by weight (w/w) of poloxamer 407.

In some embodiments, said pharmaceutically acceptable aqueous solution comprises approximately 15% to 25% by weight (w/w) of poloxamer 407, and wherein said gamma secretase inhibitor is present in approximately 0.1% to 5% w/v, and is selected from crystalline (2,2,3,3,3-pentafluoropropyl)-carbamic acid (S)-1-((S)-6-oxo-6,7-dihydro-5H-dibenzo[b,d]azepin-7-ylcarbamoyl) ethyl ester, crystalline (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, and pharmaceutically acceptable salts of any of the foregoing.

Some embodiments provide the use of a gamma secretase inhibitor, a gamma secretase modulator, or a pharmaceutically acceptable salt of any of the foregoing, for treating cochlear synaptopathy. In some embodiments, said cochlear synaptopathy is hidden hearing loss. In some embodiments, said cochlear synaptopathy is tinnitus.

Some embodiments provide the use of a gamma secretase inhibitor, a gamma secretase modulator, or a pharmaceutically acceptable salt of any of the foregoing, for treating hearing loss resulting from loss of inner hair cell afferent synapses.

Some embodiments provide the use of a gamma secretase inhibitor, a gamma secretase modulator, or a pharmaceutically acceptable salt of any of the foregoing, for treating tinnitus resulting from loss of inner hair cell afferent synapses.

Some embodiments provide the use of a gamma secretase inhibitor, a gamma secretase modulator, or a pharmaceutically acceptable salt of any of the foregoing, for treating hearing loss, wherein said hearing loss is characterized by a normal ABR threshold and/or a normal DPOAE. In some embodiments, said hearing loss is characterized by sustained deficits in ABR wave 1 amplitude.

Some embodiments comprise the use of a gamma secretase inhibitor or a pharmaceutically acceptable salt thereof.

Some embodiments comprise the use of a gamma secretase modulator or a pharmaceutically acceptable salt thereof. In some embodiments, said gamma secretase modulator, or a pharmaceutically acceptable salt thereof, selected from the group consisting of:

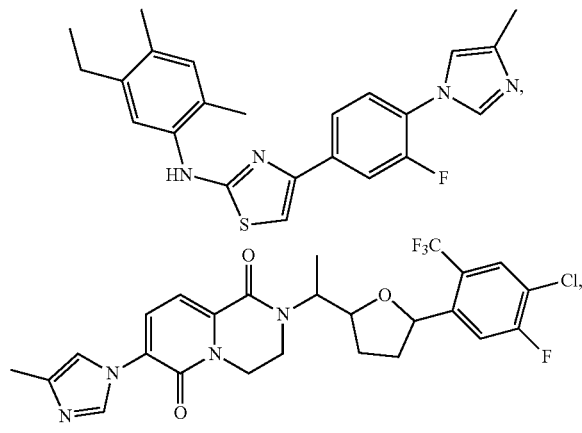

and pharmaceutically acceptable salts of any of the foregoing.

Some embodiments comprise the use of a gamma secretase inhibitor or a pharmaceutically acceptable salt thereof. In some embodiments, said gamma secretase inhibitor, or a pharmaceutically acceptable salt thereof, is selected from the group consisting of: (2,2,3,3,3-pentafluoropropyl)-carbamic acid (S)-1-((S)-6-oxo-6,7-dihydro-5H-dibenzo[b,d]azepin-7-ylcarbamoyl) ethyl ester and (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide or a pharmaceutically acceptable salt of any of the foregoing.

In some embodiments, said use comprises administering said gamma secretase inhibitor, gamma secretase modulator, or a pharmaceutically acceptable salt of any of the foregoing, to or near the round window of the cochlea.

In some embodiments, said use comprises administering said gamma secretase inhibitor, gamma secretase modulator, or a pharmaceutically acceptable salt of any of the foregoing, via the oral route.

In some embodiments, said use comprises administering said gamma secretase inhibitor, gamma secretase modulator, or a pharmaceutically acceptable salt of any of the foregoing, intratympanically.

Some embodiments comprise the use of a gamma secretase modulator. In some embodiments, said gamma secretase modulator, or a pharmaceutically acceptable salt thereof, is selected from the group consisting of:

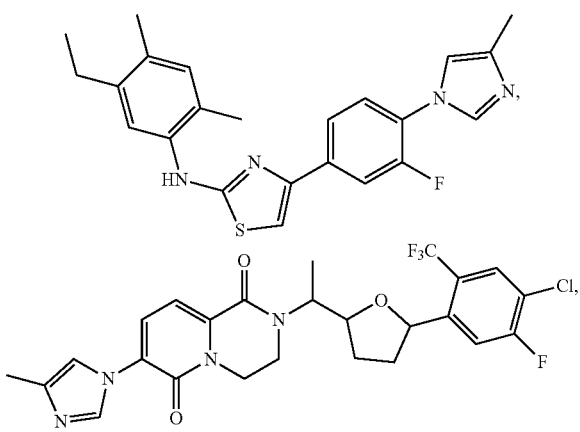

and pharmaceutically acceptable salts of any of the foregoing.

Some embodiments comprise the use of a gamma secretase inhibitor. In some embodiments, said gamma secretase inhibitor, or a pharmaceutically acceptable salt thereof, is selected from the group consisting of: (2,2,3,3,3-pentafluoropropyl)-carbamic acid (S)-1-((S)-6-oxo-6,7-dihydro-5H-dibenzo[b,d]azepin-7-ylcarbamoyl) ethyl ester, (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, and pharmaceutically acceptable salts of any of the foregoing.

Some embodiments comprise the use of a gamma secretase modulator. In some embodiments, said gamma secretase modulator, or a pharmaceutically acceptable salt thereof, is selected from the group consisting of:

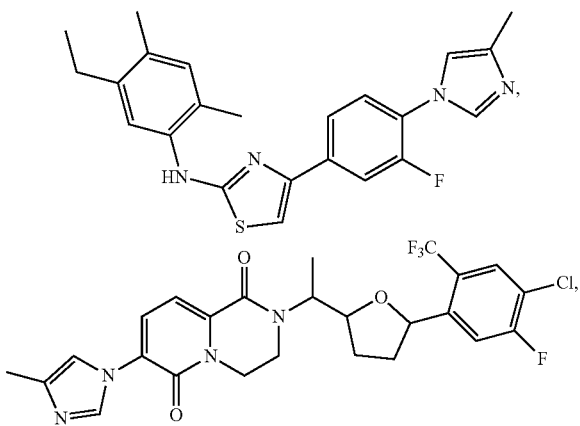

and pharmaceutically acceptable salts of any of the foregoing.

Some embodiments comprise the use of a gamma secretase inhibitor, or a pharmaceutically acceptable salt thereof. In some embodiments, said gamma secretase inhibitor, or a pharmaceutically acceptable salt thereof, is selected from the group consisting of: (2,2,3,3,3-pentafluoropropyl)-carbamic acid (S)-1-((S)-6-oxo-6,7-dihydro-5H-dibenzo[b,d]azepin-7-ylcarbamoyl) ethyl ester, (2R)-2-fluoro-2-methyl-N—[(S)-5-methyl-6-oxo-6,7-dihydro-5H-dibenzo[b,d]azepin-7-yl]-N'-(2,2,3,3,3- pentafluoropropyl)malonamide, and pharmaceutically acceptable salts of any of the foregoing.

Some embodiments comprise the use of a gamma secretase modulator. In some embodiments, said gamma secretase modulator selected from the group consisting of:

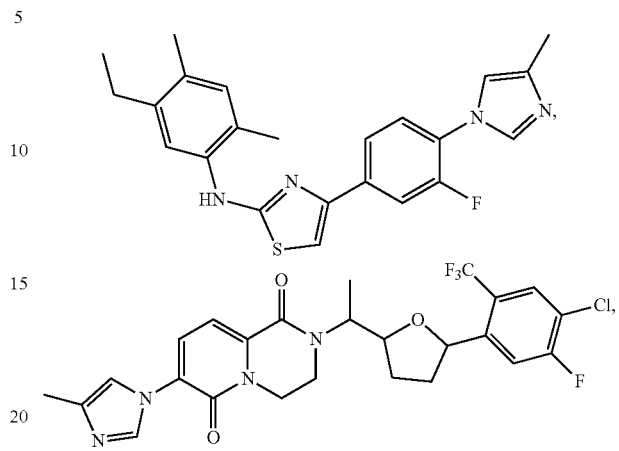

and pharmaceutically acceptable salts of any of the foregoing.

Some embodiments comprise the use of a gamma secretase inhibitor, or a pharmaceutically acceptable salt thereof. In some embodiments, said gamma secretase inhibitor selected from the group consisting of: (2,2,3,3,3-pentafluoropropyl)-carbamic acid (S)-1-((S)-6-oxo-6,7-dihydro-5H-dibenzo[b,d]azepin-7-ylcarbamoyl) ethyl ester, (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, and pharmaceutically acceptable salts of any of the foregoing.

In some embodiments, said gamma secretase inhibitor, or a pharmaceutically acceptable salt thereof, is formulated as a pharmaceutical composition comprising a pharmaceutically acceptable aqueous solution comprising:
  (A) approximately 15% to 25% by weight (w/w) of poloxamer 407; or
  (B) (i) approximately 15% to 25% by weight (w/w) of poloxamer 407 and (ii) approximately 0.5% to 4% by weight (w/w) of hydroxypropyl methylcellulose having a nominal viscosity of 40-60 cP or grade 80-120 cP; or
  (C) (i) approximately 10%-20% by weight (w/w) of poloxamer 407, and (ii) approximately 0.1%-0.3% by weight (w/w) of Carbopol® 974P; or
  (D) (i) approximately 0.5% to 8% by weight (w/w) of a hyaluronic acid; or
  (E) (i) approximately 0.5% to 4% by weight (w/w) of a hyaluronic acid, and (ii) approximately 5% to 20% by volume of polyethylene glycol 400;
wherein said gamma secretase inhibitor is present in approximately 0.01% to about 20% w/v of said aqueous solution.

In some embodiments, said gamma secretase inhibitor is selected from crystalline (2,2,3,3,3-pentafluoropropyl)-carbamic acid (S)-1-((S)-6-oxo-6,7-dihydro-5H-dibenzo[b,d] azepin-7-ylcarbamoyl) ethyl ester, crystalline (2R)-2-fluoro-2-methyl-N—[(S)-5-methyl-6-oxo-6,7-dihydro-5H-dibenzo [b,d]azepin-7-yl]-N'-(2,2,3,3,3- pentafluoropropyl) malonamide, and pharmaceutically acceptable salts of any of the foregoing.

In some embodiments, said pharmaceutically acceptable aqueous solution comprises approximately 15% to 25% by weight (w/w) of poloxamer 407.

In some embodiments, said pharmaceutically acceptable aqueous solution comprises approximately 15% to 25% by weight (w/w) of poloxamer 407, and wherein said gamma secretase inhibitor is present in approximately 0.1% to 5% w/v, and is selected from crystalline (2,2,3,3,3-pentafluoropropyl)-carbamic acid (S)-1-((S)-6-oxo-6,7-dihydro-5H-dibenzo[b,d]azepin-7-ylcarbamoyl) ethyl ester, crystalline (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, and pharmaceutically acceptable salts of any of the foregoing.

BRIEF DESCRIPTION OF THE FIGURES

FIGS. 1A, 1B, 1C and 1D depict the anatomy of an ear, cross section of the cochlea, the organ of Corti, and inner hair cell afferent synapses, respectively.

DETAILED DESCRIPTION

Figure 2A:
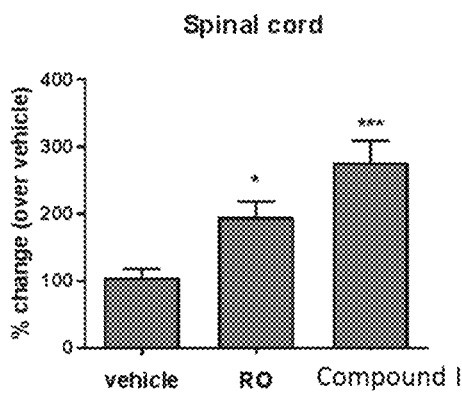
FIGS. 2A and 2B show increases of DCC α-fragment levels of GSM- and GSI-treated spinal cord and cochlea over vehicle treated samples, respectively.

"Cochlear (or auditory) synaptopathy" refers to loss of synapses between inner hair cells and cochlear afferent nerve fibers, and may be manifested as various hearing impairments, including for example:

sensorineural hearing loss such as age-related hearing loss (also known as presbycusis), noise-induced hearing loss (including exposure to a sudden loud noise, and prolonged or repeated exposure to loud noises), ototoxin-induced hearing loss (ototoxins include aminoglycoside antibiotics such as gentamicin, kanamycin, amikacin, and platinum chemotherapeutic agents such as cisplatin), and speech-in-noise hearing loss (hidden hearing loss; difficulties in understanding speech in noisy environments);

tinnitus (perception of phantom sound in the absence of external sound, or ringing in the ears);

hyperacusis (collapsed tolerance to normal environmental sound); and

Meniere's Disease (an inner ear disorder characterized by fluctuating threshold shifts, vertigo and tinnitus).

Patients suffering from cochlear synaptopathy generally cannot be diagnosed using audiometric threshold tests and may exhibit normal auditory brainstem response (ABR) (an auditory evoked neural potential recorded by electrodes placed on the scalp). This is because noise-induced auditory nerve damage may be present even after the recovery of ABR threshold (Furman et al. *Journal of Neurophysiology* 2013 110(3):577-586) and more generally, threshold assessments such as audiograms (hearing tests) are useful in detecting outer hair cell damage rather than damage to the auditory nerve and synapses (Kujawa et al. 2009). Patients with cochlear synaptopathy may exhibit reduced amplitudes of the ABR wave I potential relative to patients not having cochlear synaptopathy. (Schaette et al. 2011). Some patients with cochlear synaptopathy may exhibit decreased amplitude in ABR wave I amplitude in their audiograms, relative to patients not having cochlear synaptopathy. Recent study also suggests that the SP/AP ratio (summating potential/action potential) obtained from electrocochleography may be a useful detection/diagnostic tool, wherein an elevated SP/AP ratio compared to a reference ratio is indicative of cochlear synaptopathy (Liberman M C, et al., *PloS ONE,* 2016, 11(9):e0162726; and WO2017127619). High frequency audiometry measuring high frequency thresholds, greater than 8 kHz or in the range between 8 and 16 kHz, has been suggested as a way of identifying cochlear synaptopathy (Liberman et al. 2016).

The latency of ABR wave-V in noise may also be used as a diagnostic marker as it has been demonstrated to reflect auditory nerve loss (Mehraei G, et al., *J. Neurosci.* 2016, 36(13): 3755-64). Cochlear synaptopathy may also be detected or diagnosed using word recognition in noise or with time compression and reverberation. The hearing-in-noise test and speech-in-noise test may be used to identify patients with cochlear synaptopathy. Examples of word recognition performance test including the Northwestern University Auditory Test No. 6 (NU-6), the Central Institute of the Deaf (CID) W-22 test, the Northwestern University Children's Perception of Speech test (NU-CHIPS), City University of New York Nonsense Syllable test, the Nonsense Syllable test, the Hearing In Noise Test (HINT), the QuickSIN, the Synthetic Sentence Identification test (SSI), the Speech Perception and Noise test (SPIN), and the Connected Speech test. Thus cochlear synaptopathy such as hidden hearing loss may be detected and or diagnosed using one or a combination of the aforementioned tools.

Gamma secretase inhibitors and gamma secretase modulators have been long studied as potential therapeutic agents for Alzheimer's disease and cancer, and a large number of such compounds have been reported, particularly in the patent literature.

Gamma Secretase Inhibitors (GSI)

WO 2014/039781, entitled "Treating Hearing Loss," discloses method for treating hearing loss associated with loss of cochlear hair cells using Notch inhibitors, e.g., gamma secretase inhibitors. Generally, gamma-secretase inhibition leads to the inhibition of Notch signaling to the nucleus, resulting in the de-repression of the Atoh1 enhancer element and subsequent induction of ATOH1, a key regulator of hair cell differentiation. Although Notch signaling has been shown to be involved in the generation of new inner ear sensory hair cells the same link has not been made with respect to synapse formation. We have evaluated gamma secretase inhibitors that inhibit Notch signaling as well as those that do not inhibit Notch signaling, so called Notch sparing gamma secretase inhibitors, in regenerating IHC afferent synapses. Our findings indicate that both types of GSIs are equally effective, suggesting that gamma secretase inhibition but not Notch inhibition is the likely mechanism for regenerating synapses in the inner ear.

Examples of suitable gamma-secretase inhibitors for use in any of the methods of the present disclosure are disclosed, for instance, in U.S. Patent Application Publication Nos. 2004/0029862, 2004/0049038, 2004/0186147, 2005/0215602, 2005/0182111, 2005/0182109, 2005/0143369, 2005/0119293, 2008/008316, and 2011/0020232; U.S. Pat. Nos. 6,756,511; 6,890,956; 6,984,626; 7,049,296; 7,101,895; 7,138,400; 7,144,910; 7,160,875; 7,166,587; 7,183,303; 7,253,158; 8,188,069; 8,084,477; International Publication Nos. WO 1998/28268; WO 2001/70677; WO 2002/049038, WO 2004/186147, WO 2003/093253, WO 2003/093251, WO 2003/093252, WO 2003/093264, WO 2005/030731, WO 2005/014553, WO 2004/039800, WO 2004/039370, and WO2017/007702; and EP2244713, the disclosures, each of which is hereby incorporated by reference in its entirety. Some specific gamma secretase inhibitors that may be mentioned include: (2,2,3,3,3-pentafluoropropyl)-carbamic acid (S)-1-((S)-6-oxo-6,7-dihydro-5H-dibenzo[b,d]azepin-7-ylcarbamoyl) ethyl ester (referred to as "Compound I" herein); (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide (referred to as "Compound II" herein); 4,4,4-trifluoro-N-((2S)-1-((9-methoxy-3,3-dimethyl-5-oxo-2,3,5,6-tetrahydro-1H-benzo[f]pyrrolo[1,2-a]azepin-6-yl)amino)-1-oxopropan-2-yl)butanamide (referred to as "Compound X" herein); DAPT; L-685458; avagacestat; BMS-299897; MK-0752; YO-01027; LY411575; ELN-46719; PF-03084014; semagacestat; begacestat; MRK-003; MRK-560; RO-4929097; JLK 6; ALX-260-127.

In some embodiments, the gamma secretase inhibitor for use in any of the methods of the present disclosure is (2,2,3,3,3-pentafluoropropyl)-carbamic acid (S)-1-((S)-6-oxo-6,7-dihydro-5H-dibenzo[b,d]azepin-7-ylcarbamoyl) ethyl ester or (2R)-2-fluoro-2-methyl-N—[(S)-5-methyl-6-oxo-6,7-dihydro-5H-dibenzo[b,d]azepin-7-yl]-N'-(2,2,3,3,3- pentafluoropropyl)malonamide.

Gamma Secretase Modulators (GSM)

Gamma secretase modulators (GSMs) are small molecule compounds that selectively reduce the formation of pathogenic amyloid beta 42 peptide (A42) without affecting the total amount of AB production (Weggen S, et al., Nature. 2001, 414, 212-214), and have emerged as promising therapeutics for the treatment of Alzheimer's disease. This class of small molecules is a significant departure from gamma secretase inhibitors (GSIs) that function as protease inhibitors reducing gamma secretase activity leading to a reduction in total AB production. GSIs were discovered to have mechanism based toxicity directly related to the inhibition of NOTCH processing. More recently NOTCH sparing GSI have been described (Fraering P C, et al., *J. Biol. Chem.*, 2005, 280(51):41987-96); however, whether they have sufficient selectivity over NOTCH signaling to avoid toxicity remains to be seen. In contrast, GSMs typically offer much high selectivity for AB42 lowering over NOTCH inhibition, and thus may potentially avoid toxicities associated with GSIs at therapeutic levels. GSMs may be identified using screening methods known in the art, such as those described in Chen et al., *Bioorg. Med. Chem. Lett.*, 2013, 23:6447-6454, and Jung, et al., *FASEB J.* 2013, 27(9):3775-3785. Although GSMs have been described for the treatment of Alzheimer's disease their use for the treatment of hearing loss has not been reported. Furthermore their use for the treatment of hearing loss would not at all be expected or predicted by any current available data in the literature.

Examples of suitable gamma-secretase modulators for use in any of the methods of the present disclosure are disclosed, for instance, in Bursavich et al, *J. Med. Chem.*, 2016, 59:7389-7409; Crump et al, *Biochem.*, 2013, 52(19): 3197-216; as well as references cited therein. Other publications that disclose gamma secretase modulators are, e.g., U.S. Pat. No. 7,244,739, WO201507058, WO2016201168, WO2014045156, WO2012116965, US20150274721, each of which is hereby incorporated by reference in its entirety. Some gamma secretase modulators that may be named are provided in FIG. 11.

In some embodiments, the gamma secretase modulator for use in any of the methods of the present disclosure is selected from:

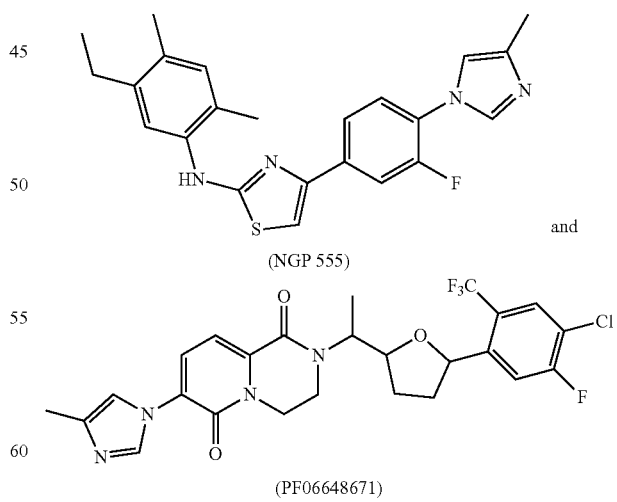

(NGP 555)

(PF06648671)

and pharmaceutically acceptable salts of any of the foregoing.

In some embodiments, the gamma secretase modulator for use in any of the methods of the present disclosure is:

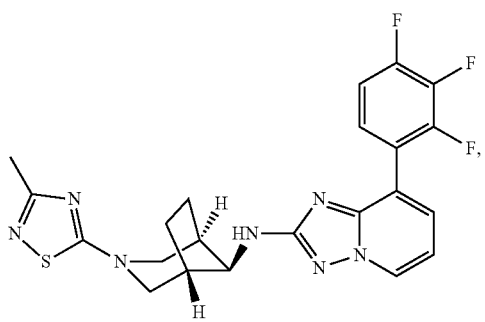 [SMILES: Cc1nsc(N2C[C@H]3CC[C@@H](C2)[C@@H]3Nc2nc3c(-c4ccc(F)c(F)c4F)cccn3n2)n1]

and pharmaceutically acceptable salts thereof.

GSI/Ms may be evaluated for the use of the present disclosure using in vitro and/or in vivo assays known in the art, such as those described in the Examples; namely, in vitro assay to measure SGN neurite growth following exposure to GSI/Ms; in vivo assays to assess restoration of synaptic densities following treatment with GSI/Ms in noise-induced and ototoxin-induced synaptopathy in mice and guinea pigs, respectively.

Pharmaceutical Compositions

Pharmaceutical compositions typically include a pharmaceutically acceptable carrier. The term "pharmaceutically acceptable carrier" refers to a carrier or adjuvant that may be administered to a patient, together with a compound of this invention, or a pharmaceutically acceptable salt thereof, and which does not destroy the pharmacological activity thereof and is nontoxic when administered in doses sufficient to deliver a therapeutic amount of the compound.

The term "composition" as used herein is intended to encompass a product comprising the specified ingredients, as well as any product which results, directly or indirectly, from combination of the specified ingredients. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof.

The pharmaceutical compositions may be formulated for administration systemically such as orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), via an implanted reservoir, or by injection. The pharmaceutical compositions may be formulated for local administration to optimize drug exposure locally while limiting systemic exposure.

In some embodiments, the active ingredients of the present disclosure are administered at about 0.01 mg to 1,000 mg, about 2 mg to 900 mg, about 3 mg to 800 mg, about 4 mg to 700 mg, about 5 mg to 600 mg, about 10 mg to 500 mg, about 50 mg to 400 mg, about 100 mg to 300 mg, about 150 mg to 250 mg, or any value in between. In some embodiments, the total daily dosage may be divided and administered in portions during the day, for example, once per day, twice per day, three times per day or four times per day. In some embodiments, the total dosage may be administered once per week, twice per week, three times per week, four times per week, five times per week or six times per week; the frequency of administration may be reduced to, for example, once biweekly, once monthly, once quarterly, and the like when sustained release compositions are used.

In some embodiments, the pharmaceutical compositions of the present disclosure for injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

In some embodiments, the pharmaceutical compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminum monostearate and gelatin. If desired, and for more effective distribution, the compounds can be incorporated into slow release or targeted delivery systems such as polymer matrices, liposomes, and microspheres.

In some embodiments, the pharmaceutical compositions that are injectable formulations can be sterilized, for example, by filtration through a bacterial-retaining filter, or by incorporating sterilizing agents in the form of sterile solid pharmaceutical compositions that can be dissolved or dispersed in sterile water or other sterile injectable medium just prior to use.

In some embodiments, solid dosage forms of the instant pharmaceutical compositions for oral administration. In some embodiments, the oral dosage forms include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid pharmaceutical compositions of a similar type may also be employed as fillers in soft and hard-filled gelatin capsules using such excipients as lactose or milk sugar as well as high molecular weight polyethylene glycols and the like.

The solid dosage forms of the instant pharmaceutical compositions of tablets, dragées, capsules, pills, and granules can be prepared with coatings and shells such as enteric coatings and other coatings well known in the pharmaceutical formulating art. They may optionally contain opacifying agents and can also be of a formulation that they release the active ingredient(s) only, or preferentially, in a certain part of the intestinal tract, optionally, in a delayed manner. Examples of embedding pharmaceutical compositions which can be used include polymeric substances and waxes.

The active compounds can also be in microencapsulated form, if appropriate, with one or more of the above-mentioned excipients.

Some embodiments provide liquid dosage forms of the instant pharmaceutical compositions for oral administration. In some embodiments, the liquid dosages include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral pharmaceutical compositions can also include adjuvants such as wetting agents, emulsifying and suspending agents, sweetening, flavoring, and perfuming agents.

Suspensions of the instant compounds, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

In some embodiments the pharmaceutical compositions of the present disclosure are formulated for delivery to the inner ear. Drug delivery to the inner ear has been reviewed in the following, the contents of which are hereby incorporated by reference:
1. Salt A N and Plontke S K R, Local Inner-Ear Drug Delivery and Pharmacokinetics. *Drug Discovery Today*, 2005, 10(19): 1299-1306.
2. Liu et al., Current Strategies for Drug Delivery to the Inner Ear. *Acta Pharmaceutica Sinica* B, 2013, 3(2):86-96.
3. Leary Swan E E et al., Inner Ear Drug Delivery for Auditory Applications. *Adv Drug Deliv Rev*, 2008, 60(15):1583-1599.

In some embodiments the pharmaceutical compositions of the present disclosure are formulated for intratympanic administration such as a liquid or gel formulation to be delivered to or near the round window membrane of the cochlea. In some embodiments the pharmaceutical compositions for intratympanic administration provide sustained release of the active agent in the middle ear. Sustained release formulations typically include a polymer; suitable polymers for the present disclosure that may be mentioned include, but are not limited to, gelatin, hyaluronic acid/hyaluronates, chitosan, and polyoxyethylene-polyoxypropylene triblock copolymers [see e.g., Liu et al., *Acta Pharmaceutica Sinica B*, 2013, 13(2): 86-96, and Swan et al., *Adv. Drug Deliv. Rev.*, 2008, 60(15):1583-1599].

In some embodiments the present pharmaceutical compositions can be delivered to the middle ear as a lower viscosity liquid at ambient temperature which forms in situ a gel having a higher viscosity. The advantages of such a composition include (1) the convenience of handling a liquid at the time of administration, and (2) once gelled in situ a prolonged time of release of the drug at the site of deposit. Increasing the release time results in a prolonged time of therapeutic effectiveness and potentially lowered drug dose. Such compositions advantageously comprise a thermoreversible gel which has the property of being a liquid at ambient temperature and a gel at about mammalian body temperature.

Thermoreversible gels that are suitable for pharmaceutical application may be prepared using polymers including poly(lactic acid)-poly(ethylene glycol) (PLA-PEG) or triblock copolymers of PEG-PLGA-PEG. A chitosan-glycerolphosphate solution is able to form a reversible thermosetting gel. Addition of sugar-based phosphates transforms chitosan into a thermo-reversible gel drug delivery system. A common group of thermoreversible gels is polyoxyalkylene based polymers, such as the polyoxyethylene-polyoxypropylene triblock copolymers known generically as poloxamers. Poloxamers in aqueous solutions exhibit thermoreversible properties that are advantageous for the present disclosure. Thus, aqueous solutions of poloxamer can transition from liquid state to gel state with rising temperature. The liquid-gel transition temperature may be adjusted by varying the concentration of the poloxamer as well as addition of other excipients such as viscosity modifying agents; thus solutions of poloxamer may be prepared that are in liquid state at room temperature or below, and transition to gel state at body temperature. In some embodiments of the present composition, the thermoreversible gel is poloxamer 407 (e.g., Pluronic® F127 marketed by BASF, Florham Park, N.J.). The poloxamer may be present in a concentration from about 15 to about 25% by weight, or any value in between. In some embodiments the poloxamer 407 concentration is from about 15 to about 18% by weight, or any value in between. In some embodiment the poloxamer 407 concentration is from about 16 to about 17% by weight, or any value in between. In some embodiments the poloxamer is present in approximately 15 or 16 or 17 or 18% by weight, or any value in between. In some embodiments the pharmaceutical compositions of the present disclosure comprising poloxamer 407 may optionally include hydroxypropyl methylcellulose (HPMC) having a nominal viscosity of 40 to 120 centipoise (cP), or any value in between, and in an amount approximately 0.5% to 4% by weight, or any value in between.

In some embodiments the composition of the present disclosure is an aqueous pharmaceutical composition for intratympanic administration comprising an active agent and a pharmaceutically acceptable carrier comprising (a) approximately 0.5% to 8% by weight of a hyaluronic acid; or (b) (i) approximately 0.5% to 4% by weight of a hyaluronic acid, and (ii) approximately 5% to 20% by volume of polyethylene glycol 400 (PEG400).

In the aqueous pharmaceutical compositions for intratympanic administration the concentration of the active agent is generally from about 0.01% w/v to 20% w/v. This range includes the sub-range of about 0.05 w/v to about 15 w/v, about 0.1 w/v to about 10 w/v, about 0.1% w/v to about 5% w/v, or any value in between. In some embodiments the concentration of the active agent is from about 0.5% w/v to about 5% w/v, or any value in between. In some embodiments the concentration of the active agent is from about 0.5 to about 4% w/v, or any value in between. In some embodiments the concentration of the active agent is from about 1 to about 5% w/v, or any value in between. In some embodiments the concentration of the active agent is from about 1 to about to about 4%, or any value in between. In some embodiment the concentration of the active agent is about 0.5, 1.0, 1.5, 2.0, 2.5, 3.0, 3.5, 4.0, 4.5 or 5% w/v, or any value in between. In some embodiment the concentration of the active agent is about 0.1, 0.2, 0.3, 0.4, 0.5, 0.6, 0.7, 0.8, 0.9 or 1% w/v, or any value in between.

The composition disclosed herein may contain any conventional non-toxic pharmaceutically-acceptable excipients. In some embodiments, the pH of the composition is between about 6 to 8, or about 6 to 7, or about 7 to 8, or any value in between. In some embodiments the composition may include a buffer such as monosodium phosphate or disodium phosphate or a combination thereof and may be phosphate buffered saline (PBS), or a buffer such as tris(hydroxymethyl)aminomethane (TRIS). The amount of buffer may be from about 0.1 to about 0.5%, or any value in between, by weight.

In some embodiments the aqueous pharmaceutical composition of the present disclosure may include a viscosity modifier such as Carbopol® 974P (Lubrizol Advanced Materials, Cleveland, Ohio). In some embodiments the aqueous pharmaceutical composition for intratympanic administration comprises an active agent, and a pharmaceutically acceptable carrier comprising poloxamer 407 and a viscosity modifier such as Carbopol® 974P. In some embodiments poloxamer 407 is present in approximately 10% to 20% by weight, and Carbopol® 974P is present in about 0.1% to about 0.3% by weight. Other common excipients may include preservatives such as methylparaben, as well as sodium chloride to provide isotonicity. The compositions are formulated such that they provide sustained release of the active agent for a period sufficient to effectuate gamma secretase modulation. The sustained modulation of gamma secretase minimizes the frequency of administration to once weekly, biweekly, monthly, bimonthly, quarterly, semiannually, annually, etc. In some embodiments, the dosing frequency is once every two weeks, or twice a month, or monthly or once every other month, or quarterly.

The aqueous pharmaceutical composition disclosed herein comprising an active agent and a carrier may be prepared using conventional methods, and may be packaged for single dose use such as in a syringe or for multiple dose such as in a vial. Alternatively, the active agent component and the aqueous solution component may be packaged separately, in separate compartments or in separate containers, and are mixed prior to administration.

In some embodiments, any of the aqueous pharmaceutical compositions disclosed herein further comprise NT-3.

Illustrative examples of compositions suitable for local inner ear administration of gamma secretase inhibitors and gamma secretase modulators are provided in WO2017075264, which is hereby incorporated by reference. Some examples include pharmaceutical composition comprising a pharmaceutically acceptable aqueous solution comprising:
 (A) approximately 15% to 25% by weight (w/w) of poloxamer 407; or
 (B) (i) approximately 15% to 25% by weight (w/w) of poloxamer 407 and (ii) approximately 0.5% to 4% by weight (w/w) of hydroxypropyl methylcellulose having a nominal viscosity of 40-60 cP or grade 80-120 cP; or
 (C) (i) approximately 10%-20% by weight (w/w) of poloxamer 407, and (ii) approximately 0.1%-0.3% by weight (w/w) of Carbopol® 974P; or
 (D) (i) approximately 0.5% to 8% by weight (w/w) of a hyaluronic acid; or
 (E) (i) approximately 0.5% to 4% by weight (w/w) of a hyaluronic acid, and (ii) approximately 5% to 20% by volume of polyethylene glycol 400;

wherein said GSI or GSM is present in approximately 0.01% to about 20% w/v of said aqueous solution. In some embodiments, the gamma secretase inhibitor is selected from crystalline (2,2,3,3,3-pentafluoropropyl)-carbamic acid (S)-1-((S)-6-oxo-6,7-dihydro-5H-dibenzo[b,d]-azepin-7-ylcarbamoyl) ethyl ester and crystalline (2R)-2-fluoro-2-methyl-N—[(S)-5-methyl-6-oxo-6,7-dihydro-5H-dibenzo[b,d]azepin-7-yl]-N-(2,2,3,3,3-pentafluoropropyl) malonamide. In some embodiments, the gamma secretase modulator is selected from NGP 555 and PF06648671. In some embodiments the pharmaceutically acceptable aqueous solution comprises approximately 15% to 25% by weight (w/w) of poloxamer 407. In some embodiment the pharmaceutically acceptable aqueous solution comprises approximately 15% to 25% by weight (w/w) of poloxamer 407, and wherein said GSI or GSM is present in approximately 0.1% to 5% w/v, and is selected from the group consisting of crystalline (2,2,3,3,3-pentafluoropropyl)-carbamic acid (S)-1-(S)-6-oxo-6,7-dihydro-5H-dibenzo[b,d]azepin-7-ylcarbamoyl) ethyl ester, crystalline (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl) malonamide, NGP 555 and PF06648671.

Uses and Methods of Treatment

Some embodiments provide methods for the treatment of cochlear synaptopathy comprising administration of a therapeutically effective amount of a gamma secretase inhibitor, a gamma secretase modulator, or a pharmaceutically acceptable salt of any of the foregoing, to a patient in need thereof. Some embodiments provide for use of a gamma secretase inhibitor, a gamma secretase modulator, or a pharmaceutically acceptable salt of any of the foregoing, for the treatment of cochlear synaptopathy. The term "cochlear synaptopathy" generally relates to conditions resulting from loss of synapses between inner hair cells and cochlear afferent nerve fibers, regardless of the cause of such loss, and includes, but is not limited to, sensorineural hearing loss, tinnitus, hyperacusis, and Meniere's disease. Accordingly, in some embodiments, the present disclosure is directed to methods of treating hearing loss (including hidden hearing loss) or tinnitus resulting from loss of inner hair cell afferent synapses which comprises administering to a patient in need thereof a therapeutically effective amount of a gamma secretase inhibitor, a gamma secretase modulator, or a pharmaceutically acceptable salt of any of the foregoing. Similarly, in some embodiments, the present disclosure is directed to use of a gamma secretase inhibitor, a gamma secretase modulator, or a pharmaceutically acceptable salt of any of the foregoing, for treating hearing loss (including hidden hearing loss) or tinnitus resulting from loss of inner hair cell afferent synapses. As used herein hearing loss or tinnitus "resulting from loss of inner hair cell afferent synapses" include hearing loss or tinnitus that can be at least partially attributable so such loss of synapses.

Sensorineural hearing loss (SNHL) occurs from damage to the cochlea or to the neural pathway from the cochlea to the brains, and includes age-related hearing loss, noise-induced hearing loss, hearing loss caused by ototoxic chemicals, and speech-in-noise hearing loss (hidden hearing loss; difficulties in understanding speech in noisy environments).

Age-related hearing loss, or presbycusis, is progressive hearing loss that results from aging, and is usually greater at higher frequencies. Noise-induced hearing loss is caused by exposure to chronic and repeated loud noises such as loud music, heavy equipment or machinery, or by a short high intensity sound such as gunshot or explosion. Hearing loss may also be caused by ototoxic chemicals such as ototoxic drugs; known ototoxic drugs include aminoglycoside antibiotics such as gentamicin, kanamycin, amikacin; loop diuretics such as furosemide; chemotherapeutic agents such as cisplatin, carboplatin, bleomycin and vincristine. Speech-in-noise hearing loss, also known as hidden hearing loss because such hearing loss cannot be measured by the audiogram, refers to difficulties in understanding speech in noisy environments.

Tinnitus refers to a disorder characterized by the perception of sound in the absence of any external stimuli. In certain instances, tinnitus occurs in one or both ears, continuously or sporadically, and is most often described as a ringing sound. Hyperacusis refers to difficulties in tolerating normal environmental sounds; patients may such sounds unbearable and painfully loud. Meniere's Disease is an idiopathic condition characterized by sudden attacks of vertigo, nausea and vomiting that may last for 3 to 24 hours, and may subside gradually; progressive hearing loss, tinnitus and a sensation of pressure in the ears accompanies the disease through time.

In some embodiments the cochlear synaptopathy is age-related hearing loss. In some embodiments the cochlear synaptopathy is noise-induced hearing noise. In some embodiments the cochlear synaptopathy is speech-in-noise hearing loss. In some embodiments the cochlear synaptopathy is tinnitus. In some embodiments the cochlear synaptopathy is hyperacusis. In some embodiments the cochlear synaptopathy is Meniere's disease. In some embodiments the patients being treated show no obvious deficit in ABR threshold and DPOAEs, but exhibit sustained deficit in ABR wave 1 amplitude and/or wave V latency. In some embodiments, the patients being treated show elevated SP/AP ratio compared to a reference SP/AP ratio. As used herein, the term "treatment" or "therapy" or "treating" and the like includes controlling, alleviating, reversing, or slowing the progression of the condition being treated; for example, reduction or halting of further hearing loss due to the above or other factors; and the restoration of hearing following the partial or profound hearing loss due to the above or other factors. Treatment also includes prevention (e.g., delaying the onset of or reducing the risk of developing) of hearing loss as well as prophylactic use such as before, during or after receiving ototoxic chemicals such as an aminoglycoside antibiotic such as gentamicin or a platinum chemotherapeutic agent such as cisplatin.

As used herein, the term "therapeutically effective amount" refers to an amount of the active agent sufficient to elicit a desired or beneficial effect in the disease or disorder being treated; for prophylaxis, it refers to an amount of the active agent sufficient to prevent the onset or lessen the effect of the disease or disorder. The amount to be used depends on the active agent chosen, the severity of the disease or disorder being treated, the route of administration and patient characteristics such as age.

In some embodiments of the present disclosure the active agent is administered orally. In some embodiments, a gamma secretase modulator is administered in an oral pharmaceutical composition. In some embodiments, a gamma secretase inhibitor is administered in an oral pharmaceutical composition.

In some embodiments of the present disclosure the active agent is administered to the ear by intratympanic injection into the middle ear, inner ear, or cochlea or combinations thereof. Intratympanic is also referred to as transtympanic, and both terms are used interchangeably herein. Intratympanic injection is the technique of injecting a therapeutic agent through the tympanic membrane into the middle ear where the therapeutic agent may diffuse across the round window membrane to reach the inner ear. It has been used in clinical practice for many years and is a relatively minor intervention which can be carried out in a doctor's office. For repeated injections, a middle ear ventilation tube may be inserted into the tympanic membrane, through which the medication can be administered into the middle ear space behind the tympanic membrane into the middle and/or inner ear. In one embodiment, the active agent is administered intratympanically to an area near or onto the round window membrane.

In some embodiments of the present method the active agent is administered in an aqueous pharmaceutical composition comprising a thermoreversible gel; such compositions are liquid at room temperature (for ease of administration) and turn into gel at body temperature such that the pharmaceutical composition does not quickly drain through the Eustachian tube. In some embodiments the present method utilizes the pharmaceutical compositions described herein.

Doses for local middle/inner ear administration of a gamma secretase modulator, a gamma secretase inhibitor, and pharmaceutically acceptable salts of any of the foregoing, will depend on the specific compound used, the route of administration, severity of the condition being treated, and patient characteristics. The doses include from about 0.06 mg to about 100 mg. This range includes the sub-ranges of about 0.1 mg to about 90 mg, 0.25 mg to about 80 mg, 0.4 mg to 70 mg, 0.6 mg to 60 mg, 0.80 mg to 50 mg, 1.0 mg to 40 mg, 2 mg to 30 mg, and 3 mg to 20 mg. The doses may be administered in an aqueous pharmaceutical composition comprising an aqueous solution, wherein the volume of aqueous solution to be administered comprises a range of about 100 µL to about 500 µL in volume. This range of volumes includes sub-ranges of about 100 µL to 150 µL, 100 µL to 200 µL, 100 µL to 250 µL, 100 µL to 300 µL, 100 µL to 350 µL, 100 µL to 400 µL, 100 µL to 450 µL, and 100 µL to 500 µL. This range of volumes also includes sub-ranges of about 200 µL to 250 µL, 200 µL to 300 µL, 200 µL to 350 µL, 200 µL to 400 µL, 200 µL to 450 µL, and 200 µL to 500 µL. This range of volumes also includes sub-ranges of about 300 µL to 350 µL, 300 µL to 400 µL, 300 µL to 450 µL, and 300 µL to 500 µL. This range of volumes also includes sub-ranges of about 400 µL to 450 µL, and 400 µL to 500 µL. Due to physical limitations, the proportion of the active agent to the aqueous pharmaceutical composition is contemplated to be 20% by weight or less. In some embodiments, a gamma secretase inhibitor is administered to the middle/inner ear. In some embodiments, a gamma secretase modulator is administered to the middle/inner ear.

In one aspect the compounds disclosed herein may be co-administered with one or more additional agents such as a steroid; for example, dexamethasone. In some embodiments, the additional agent is NT-3. In certain embodiments, the additional agents may be administered separately from the GSI or GSM (e.g., sequentially, e.g., on different overlapping schedules). In other embodiments, these agents may be part of a single dosage form, mixed together with the GSI or GSM in a single composition. In still another embodiment, these agents can be given as a separate dose that is administered at about the same time the GSI or GSM is administered. When the compositions disclosed herein include a combination of a GSI or GSM and one or more additional therapeutic or prophylactic agents, both the GSI and GSM and the additional agent can be present at dosage levels of between about 1 to 100%, and more preferably between about 5 to 95% of the dosage administered in a monotherapy regimen.

The present disclosure is further illustrated with the following Examples which are not in any way intended to limit the scope of the claims.

Example 1. In Vitro DCC (Deleted in Colorectal Cancer) Studies with GSM and GSI

Previous reports have shown that DCC (deleted in colorectal cancer) is a γ-secretase substrate. DCC is the receptor for the guidance molecule, netrin, and its activation results in neuronal axon outgrowth, axon turning and synapse formation. Embryonic spinal cords of presenilin knockout mice treated display persistent expression of the DCC α-fragment; these fragments can enhance netrin-DCC mediated events, including axon outgrowth in cultured motor neurons (Taniguchi et al., 2003, *J. Biol. Chem.*, 278:30425-30428, and Bai et al., 2011, *Cell*, 144(1): 106-18). The following studies were performed using GSM, "RO", as well as the GSI, Compound I. RO has the structure:

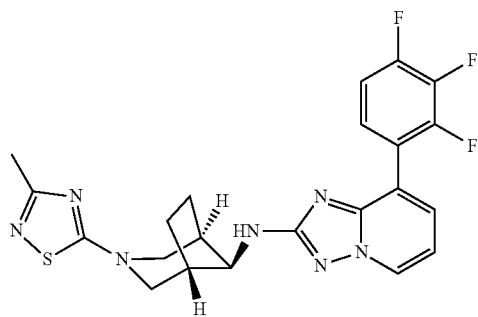 [SMILES: Cc1nsc(N2C[C@H]3CC[C@@H](C2)[C@@H]3Nc2nc3c(-c4ccc(F)c(F)c4F)cccn3n2)n1]

RO can be prepared according to the methods disclosed in WO2012116965 (e.g., using procedure analogous to that described in Example 6 therein, using as starting material the compound of Example 5, step a therein).

Mouse Ex Vivo Embryonic Spinal Cord

Spinal cords from embryonic day 15 CD-1 mice were collected and cut into 1-2 mm segments and transferred to serum-free growth media (DMEM-F12, N2 and B27 serum supplements, penicillin/streptomycin) with 1 µM RO or 1 µM Compound I. Segments were cultured for 24 h (37° C., 5% $CO_2$) then processed for Western blot. Membranes were probed with a DCC antibody recognizing the intracellular domain and bands were normalized to actin. Increase in α-fragment was observed in both the GSM and GSI treated groups compared to the vehicle group (FIG. 2a).

Mouse Ex Vivo Cochlea

Figure 2B:
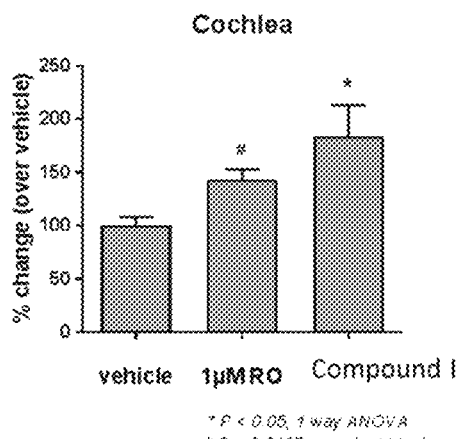

Cochleae were obtained from postnatal day 21 CD-1 mice. An opening was made in the bone at the cochlear apex to allow for fluid flow. Cochlea were incubated in serum-free growth media (DMEM-F12, N2 and B27 serum supplements, penicillin/streptomycin) with 1 µM RO or 1 µM Compound I. After 24 h, spiral ganglion were isolated and processed for Western blot. Membranes were probed with a DCC antibody recognizing the intracellular domain and bands were normalized to actin. Increase in α-fragment was observed in both the GSM and GSI treated groups compared to the vehicle group (FIG. 2b).

Example 2. GSI Increases DCC α-Fragment

Western Blot for DCC α-Fragment

Figure 3:
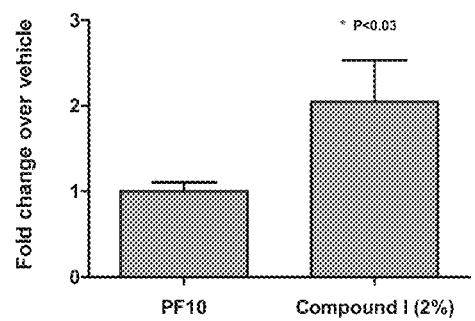
FIG. 3 shows increase of DCC α-fragment levels following in vivo application of a GSI in mice.

Compound I (2% in vehicle, 2 µl) or vehicle (2 µl) was delivered bilaterally to the round window of CBA/J mice. One week later, cochlea were collected and processed for Western blot. Both cochlea from two animals were used to generate each data point. Cochlea were homogenized in 50 µL radioimmunoprecipitation assay buffer then allowed to lyse further at 4° C. for 1 h. Bone was spun out and 4× sample loading buffer added. Samples were run on a 4-15% TGX gradient gel (BioRad, Hercules, Calif.) and transferred to a nitrocellulose membrane and blocked with Odyssey Blocking Buffer (LI-COR, NE). Blots were probed with mouse DCC (BD Biosciences, San Jose, Calif.) at 1:500, and rabbit actin (loading control) antibodies (Li-Cor, NE) in blocking buffer containing 0.1% Tween-20. Membranes were washed with PBS/0.1% Tween then incubated in secondary antibody (goat anti-mouse IRDye 680LT and goat anti-rabbit IRDye 800LT, both from LI-COR, NE) diluted 1:10,000 in blocking buffer containing 0.1% Tween-20 and 0.01% SDS. Membranes were washed in PBS then imaged on a LiCor Odyssey Classic scanner and the DCC α-fragment quantified using ImageJ. Animals treated with Compound I showed an approximately two fold increase in DCC α-fragment compared to vehicle alone (FIG. 3).

Example 3. GSMs Increase Type I Spiral Ganglion Neuron Neurite Outgrowth

Figure 4A:
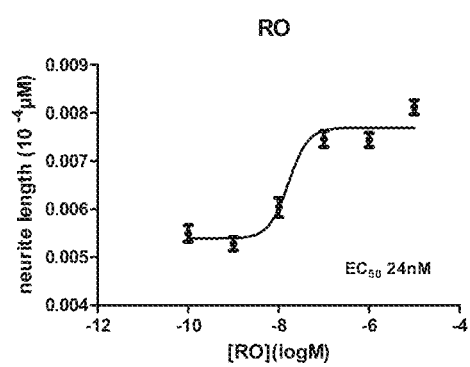
FIGS. 4A-4C show the dose-dependence increases in the lengths of Type I SGN neurites after treatment with GSMs RO, NGP555 and PF-06648671, respectively.
Figure 4B:
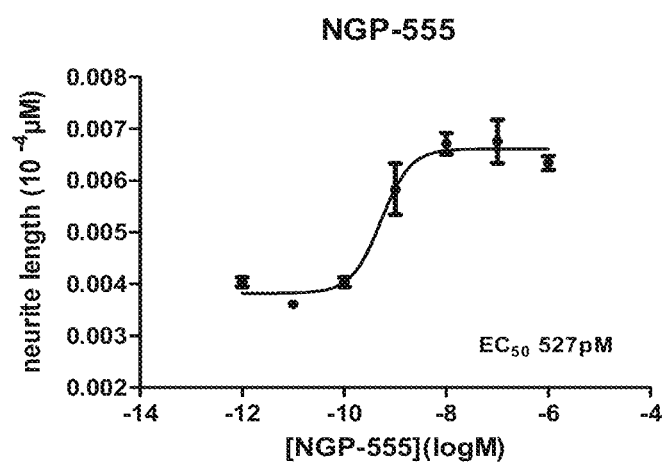
Figure 4C:
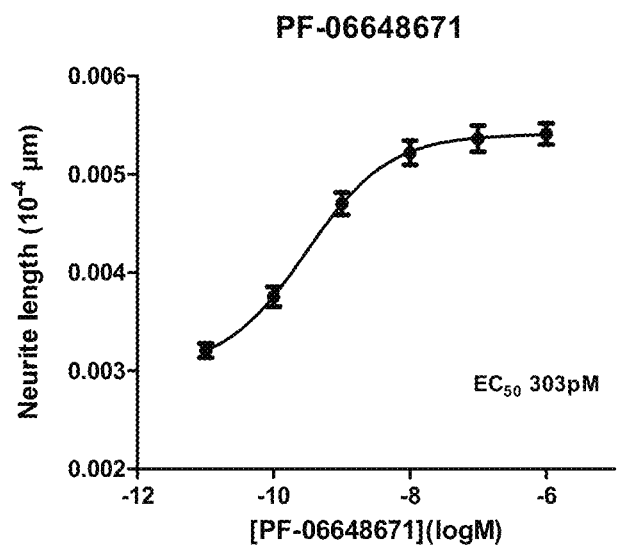

Spiral ganglion neurons (SGNs) were cultured from postnatal day 5 CD-1 mice using methods adapted from Whitlon D S, et al., *Scientific Reports*, 2015, 5, 15960, doi:10.1038/srep15960. Neurons were dissociated and plated onto collagen-coated 96-well plates in growth media (DMEM/F12, N2 and B27 serum supplements and penicillin/streptomycin). After 18 h in culture, neurons were treated with varying concentrations of RO or NGP-555 for 24 h. Neurons were fixed and stained with a rabbit b-tubulin (somato-axonal marker) antibody followed by a donkey-anti-rabbit secondary antibody conjugated to Alexa 568 and counterstained with Hoechst blue fluorescent dye to stain the DNA. Neurons were imaged on an InCell 2000. Neurite length was measured using ImageJ. Only β-tubulin$^+$ cells displaying bipolar morphology (indicative of Type I SGNs) were quantified. With either RO or NGP555, a dose dependent increase in neurite outgrowth was observed ($EC_{50}$ 24 nM for RO, $EC_{50}$ 527 pM for NGP555, FIGS. 4A and 4B, respectively). PF-06648671 was similarly evaluated and gave EC50 of 303 pM, FIG. 4C).

Figure 4D:
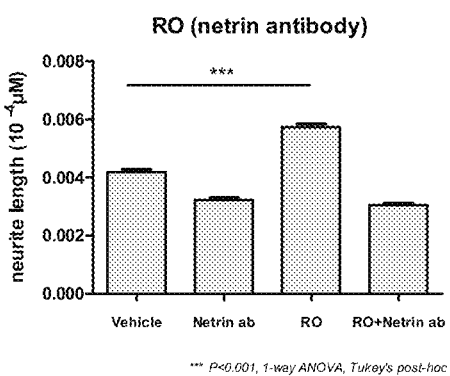
FIG. 4d shows that addition of antibody against netrin blocked the neurite lengthening effect of GSM.

To determine whether the netrin-DCC pathway is involved in GSM-induced neurite outgrowth, a function-blocking netrin antibody was applied to the media 1 h prior to addition of 1 µM test compound. After 24 h, neurons are stained with β-tubulin and only neurites from Type I neurons are analyzed. Co-application of the netrin antibody with test compound results in a significant reduction in neurite outgrowth (FIG. 4D).

Example 4. Mouse Noise-Induced Cochlear Synaptopathy

Female CBA/J mice were exposed to 98 dB 8-16 kHz filtered noise for 2 hours. Three weeks later, vehicle (0.5%

Figure 5:
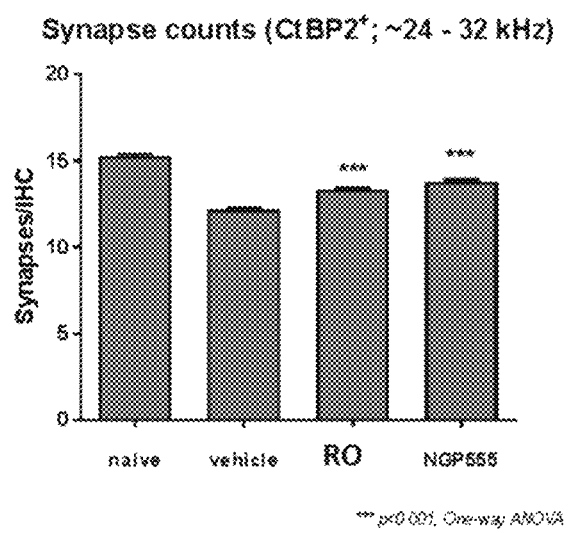
FIG. 5 shows increase in synaptic density following oral treatment of RO and NGP555 in a mouse noise-induced cochlear synaptopathy model.

Methylcellulose, b.i.d.), NGP-555 (50 mg/kg, b.i.d.) or RO (10 mg/kg, q.d.) was given by oral gavage. Fourteen days later, mice were euthanized, cochlea removed, then tissue was fixed by perfusion with 4% paraformaldehyde. Cochlea were washed with calcium/magnesium free PBS then decalcified in 12.5 mM EDTA for 3 days. Cochlea were bisected with a midmodiolar cut through the oval window to apex. Individual turns were then separated and stained with antibodies against Myo6 and CtBP2. Synapses per inner hair cell were quantified on the turn containing the 32 kHz region. Consistent with literature, a decrease in synaptic density (but no decrease in inner or outer hair cell number) was observed after the 98 dB insult. Treatment with oral NGP-555 significantly increased the number of synapses on inner hair cells (FIG. 5), demonstrating the efficacy of GSMs for the treatment of synaptopathy.

Figure 6A:
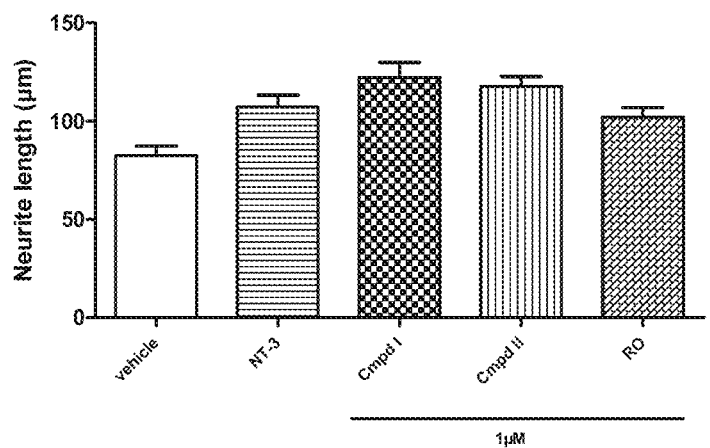
FIG. 6A shows increases of the lengths of Type I SGN neurites after treatment with GSI.
Figure 6B:
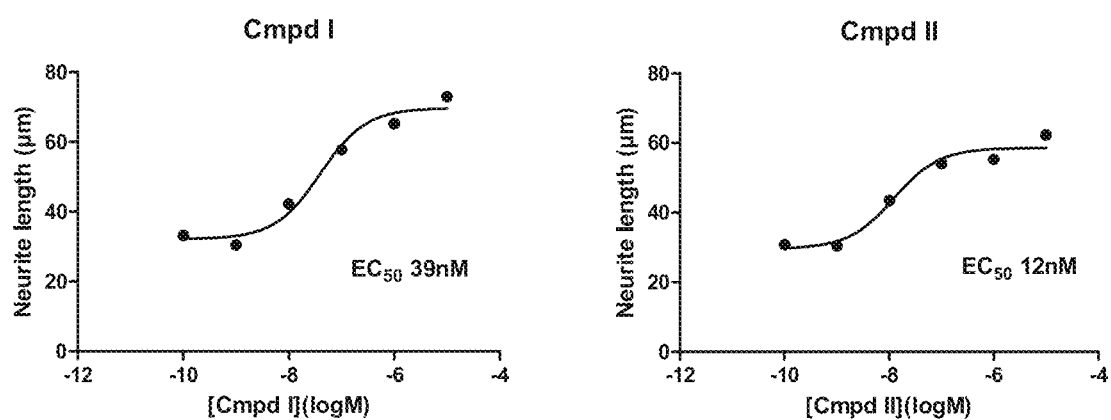
FIG. 6B shows the dose-dependence of increase in the lengths of Type I SGN neurites after treatment with gamma secretase inhibitors, Compound I and Compound II.
Figure 6C:
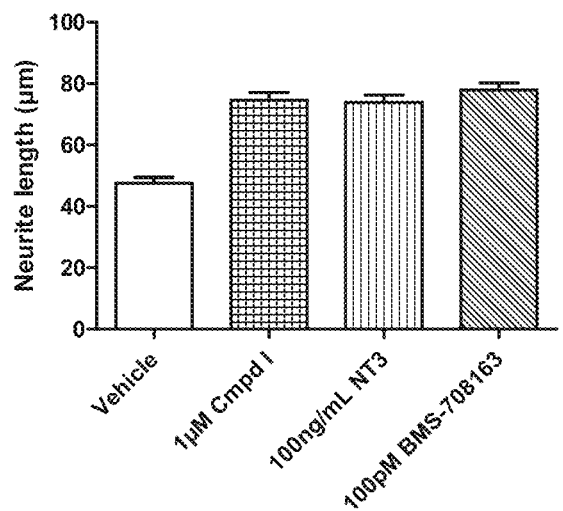
FIG. 6C shows that lengths of Type I SGN neurites increase after treatment with a Notch sparing gamma secretase inhibitor, BMS-708163 (avagacestat).
Figure 6D:
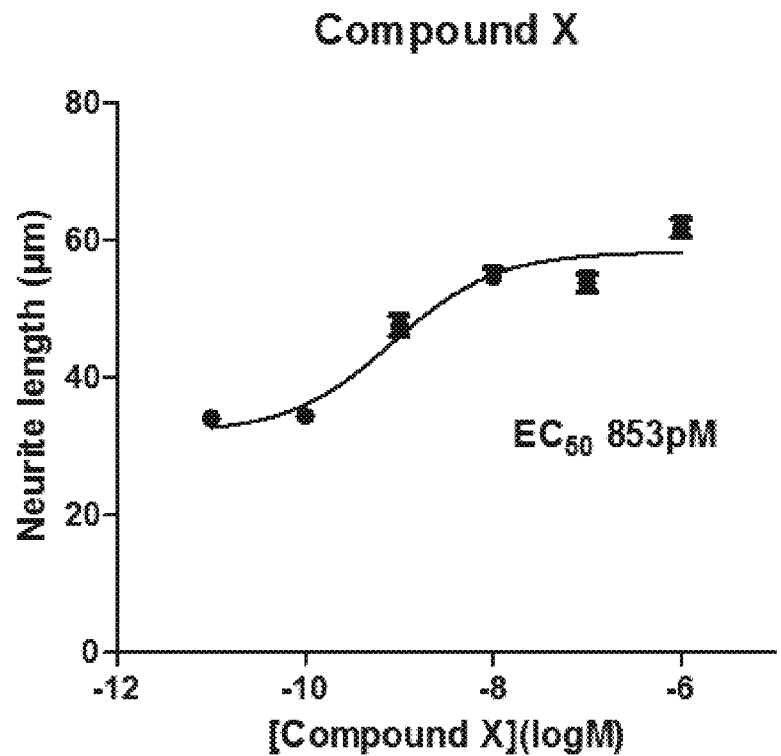
FIG. 6D shows the dose-dependence of increase in the lengths of Type I SGN neurites after treatment with a gamma secretase inhibitor, Compound X.

Example 5. Gamma Secretase Inhibitors Increase Type I Spiral Ganglion Neuron Neurite Outgrowth Mouse spiral ganglion neurons (SGN) were harvested from CD-1 mice (postnatal day 3 to 5), dissociated and cultured on collagen I in serum free media. Cells were treated for 24-48 h with test compound in 0.1% DMSO then immunostained with the neurite marker, Tuj1 and imaged. Neurite length was quantified using ImageJ software (developed by NIH and available publicly). Only Tuj1$^+$ cells with clear bipolar morphology characteristic of Type I SGNs were quantified. The test compounds were Compound I, Compound II, and RO4929097, as well as the Notch sparing GSI, BMS-708163; NT-3 was included as positive control. The results are shown in FIGS. 6A, 6B and 6C. The test compounds show a significant increase in the lengths of Type I SGN neurites in a dose-dependent manner (FIG. 6A and FIG. 6B). Moreover, BMS-708163, a Notch-sparing GSI, and Compound I, a Notch inhibiting GSI, both increased type I SGN neurite outgrowth (FIG. 6C). A further GSI, Compound X (see WO2017007702, Compound 1 therein) was evaluated in this assay, and it also show a dose-dependent increase in the lengths of Type I SGN neurites (FIG. 6D).

Example 6. Mouse Noise-Induced Cochlear Synaptopathy

Figure 7A:
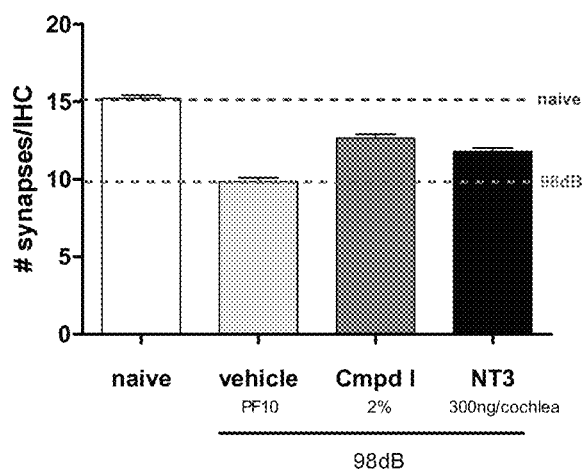
FIG. 7A shows increase in synaptic density following GSI treatment in a mouse noise-induced cochlear synaptopathy model.
Figure 7B:
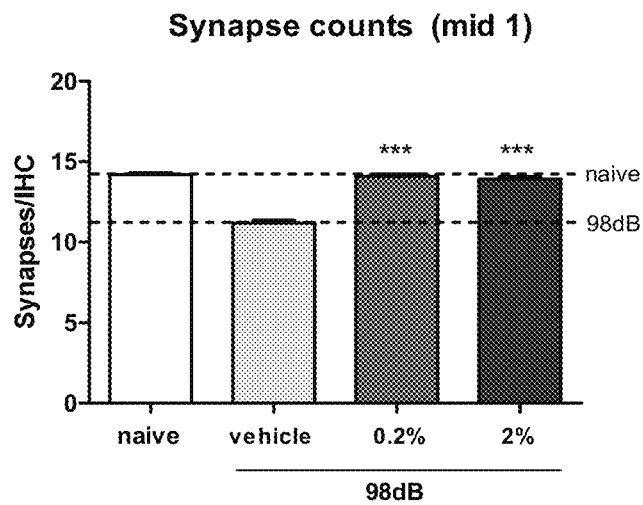
FIG. 7B shows nearly complete synapse recovery in the mid 1 region (spanning the 16-24 kHz range) following treatment with Compound I at both 0.2% and 2% dosages in a mouse noise-induced cochlear synaptopathy model.
Figure 7C:
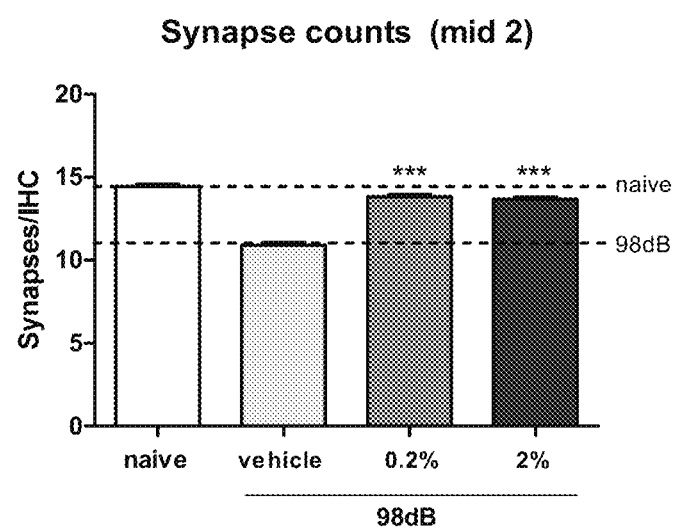
FIG. 7C shows nearly complete synapse recovery in the mid 2 region (spanning the 24-32 kHz range) following treatment with Compound I at both 0.2% and 2% dosages in a mouse noise-induced cochlear synaptopathy model.
Figure 8:
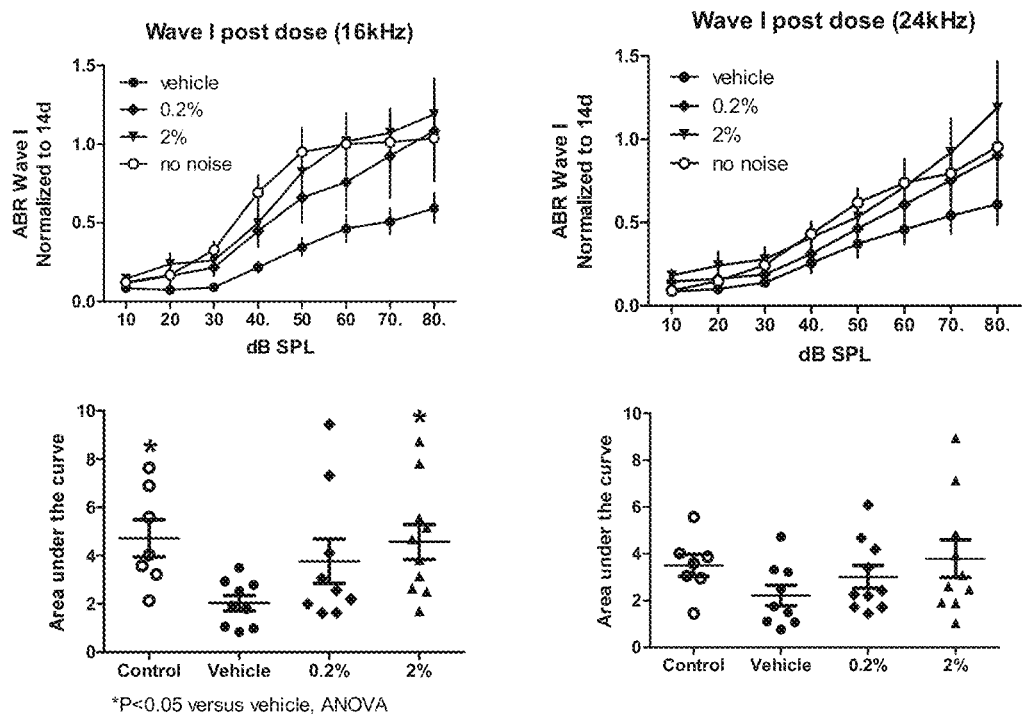
FIG. 8 shows local administration of Compound I improved wave I amplitudes following noise induced synaptopathy in mice.

Two separate experiments were conducted using this protocol: in Experiment 1 (FIG. 7A) compound I treatment was compared to NT3, in Experiment 2 (FIG. 7B, 7C and FIG. 8) we evaluated two dose levels of compound I. For both experiments female CBA/J mice 6 weeks old (The Jackson Laboratory, Bar Harbor, Me.) were exposed, awake and unrestrained, to filtered octave band noise (8-16 kHz) for 2 hours at 98 dB SPL in a reverberant sound-exposure box. Mice were placed in a custom designed wire cage sitting atop high density 4-inch foam with the wire floor 1-inch above the foam. The noise waveform was generated and filtered with a TDT RZ6 pre-amplifier (Tucker Davis Technologies, Alachua, Fla.), amplified by a Crown XLS1000 power amplifier, and delivered by JBL 2426H Compression Driver coupled to a JBL 2730A horn. Sound levels were verified in the center of the cage using a ¼-inch condenser microphone (PCB Piezotronics, Depew, N.Y.) before each exposure. ABR was collected 1 and 14 days post-noise exposure to ensure a temporary threshold shift with no permanent threshold shift. Seventeen days after noise, mice were dosed bilaterally with crystalline Compound I, (2% in PF10*) or NT3 (2 µL of 150 ng/µL) (Experiment 1); crystalline Compound I (2% and 0.2% in PF10) (Experiment 2); and ABR was collected 14 days post-dose. Vehicle control animals received bilateral injections of PF10. Age matched naïve control animals were also used.

ABR Wave I analysis: The auditory brain-stem response (ABR) waveform comprises a set of waves (labeled I-V). Mice were anesthetized with ketamine and xylazine. ABR waveforms were collected using Tucker-Davis Technologies RZ6 Auditory Processor. The stimuli used were 5 ms tone (2 ms cos 2 rise-fall) at frequencies from 4, 8, 16, 24, and 32 kHz delivered in alternating polarity at 21/s. Electrical responses were collected via needle electrodes at the vertex and at the ventral edge of the pinna with a ground reference in the center of the skull, amplified 20× with a 3-100 Hz passband, and averaged with 512 responses at each SPL. Responses were collected for stimulus levels in 10 dB steps from 90 dB SPL to 10 dB SPL. ABR threshold was defined as the lowest sound level at which a reproducible waveform could be observed. If no detectable response was observed at 90 dB SPL, the threshold was defined as 100 dB SPL. The functional measure of synaptopathy through wave I amplitudes which were expressed in volts. Wave I peak amplitudes were determined by extracting the raw waveform voltage averages and determining the window or latency at which the peak of wave I appears. Peak to trough measurements were used to calculate wave I amplitude. Post-treatment wave I amplitudes (at the selected frequencies) for each decibel level were normalized to the day 14 value to assess wave 1 amplitude.

Immunohistochemistry: Animals were sacrificed immediately following the last ABR by decapitation and processed for immunohistochemistry. Briefly, cochlea were removed and fixed by intrascalar perfusion of 4% paraformaldehyde (PFA). Cochlea were fixed overnight, then PFA exchanged for a solution of 125 mM EDTA for decalcification (at least 72 hours). Bone was removed and the organ of Corti was transected into apical (~beginning—16 kHz), mid 1 (~16-24 kHz), mid 2 (~24-32 kHz) and basal (~32 kHz—end) turns and transferred into a 96-well plate containing DBPS for immunostaining. Cochlear tissue was blocked with 5% horse serum in DPBS and 0.3% Triton X-100 for 1 hr at room temperature followed by overnight incubation at 37° C. with following primary antibodies: mouse (IgG1) anti-CtBP2 (C-terminal Binding Protein) at 1:200 (BD Biosciences), rabbit Myosin 6 at 1:250 (Proteus Biosciences, Ramona, Calif.) for delineating hair cells. Cochlear pieces were washed and then incubated for 60 min at room temperature in species-appropriate secondary antibodies: CF647 Goat Anti-Mouse IgG1 (Biotium) at 1:500, Alexa Fluor 568-conjugated donkey anti-rabbit (Thermo Fisher) at 1:500. Hoechst 33342 (Thermo Fisher) was used as a nuclear counterstain. Stained cochlear pieces were slide mounted and imaged using a Nikon C2 confocal microscope using NIS Elements software (Version 4.20, Melville, N.Y.).

Analysis: Images were taken using a 40× oil objective at 0.5 µm increments on the z-axis. CtBP2$^+$ synapses were manually quantified per inner hair cell. Inner and outer hair cells were characterized by Myosin 6 immunoreactivity and location, and were quantified manually.

Statistical Evaluation: Data were analysed using GraphPad Prism (La Jolla, Calif.) and statistical significance was determined by two-tailed Student's t test or one-way ANOVA followed by post-hoc analysis where appropriate.

Example 7. Guinea Pig Kanamycin Model

Figure 9:
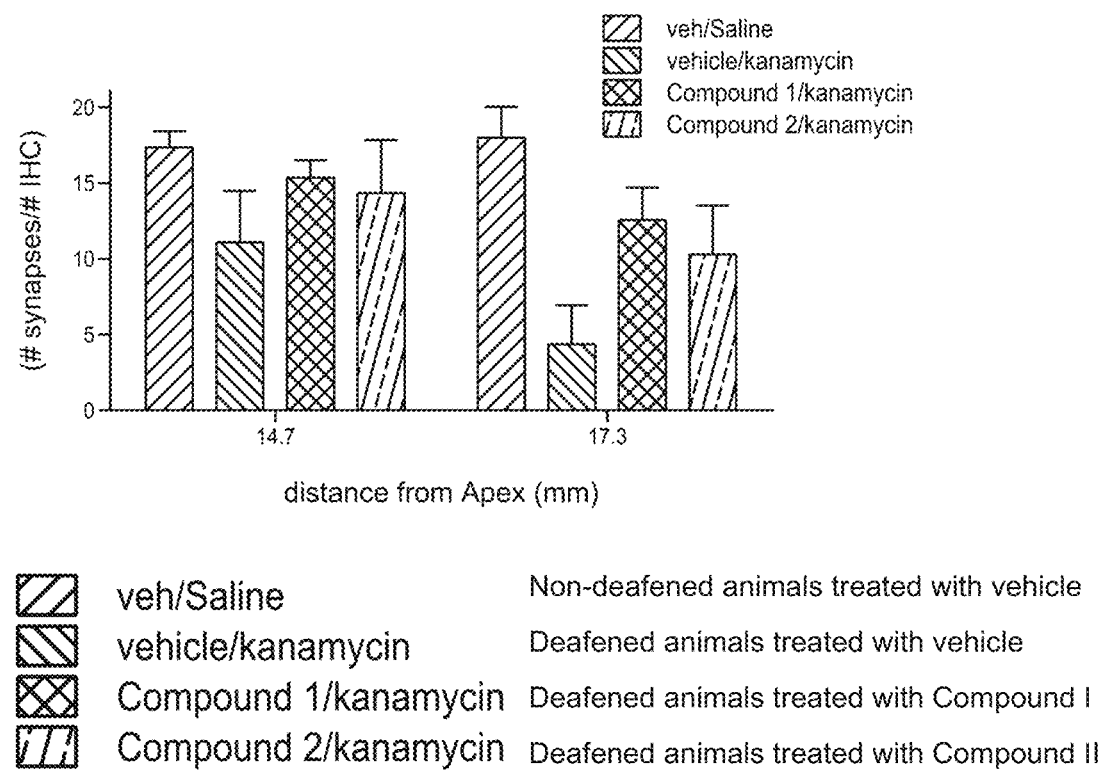
FIG. 9 shows increase in synaptic density following GSI treatment in a kanamycin-induced cochlear synaptopathy guinea pig model.
Figure 10A:
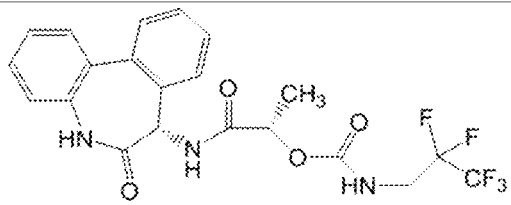
FIGS. 10A, 10B, and 10C show the structures of GSI test compounds, and additional examples of GSIs.
Figure 10A:
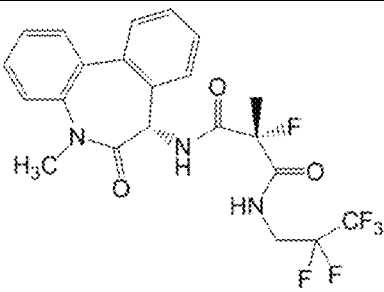
Figure 10A:
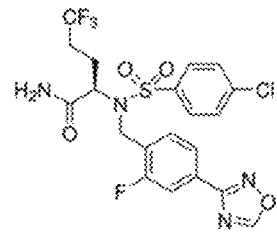
Figure 10A:
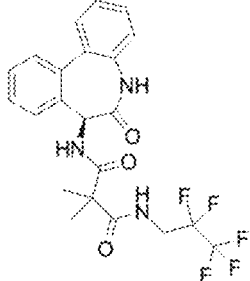
Figure 10A:
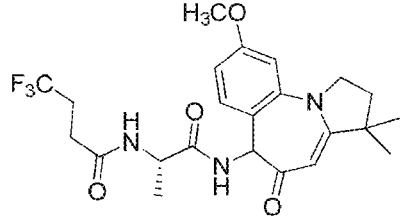
Figure 10A:
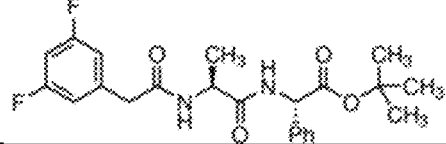
Figure 10B:
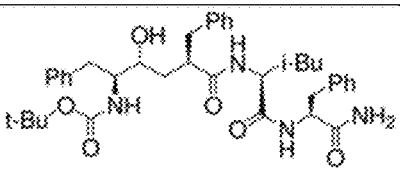
Figure 10B:
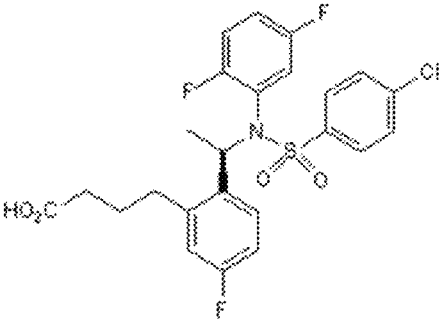
Figure 10B:
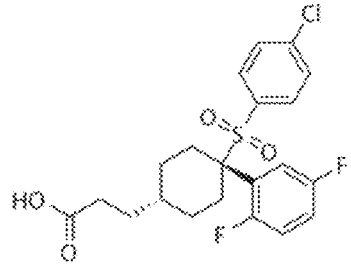
Figure 10B:
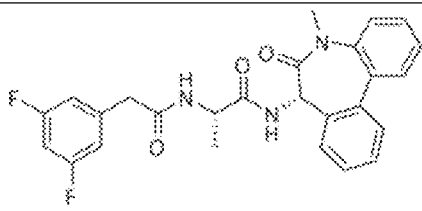
Figure 10B:
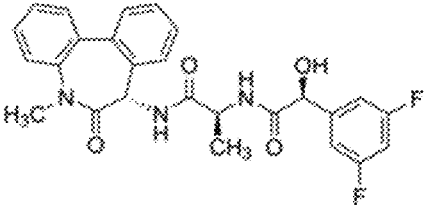
Figure 10B:
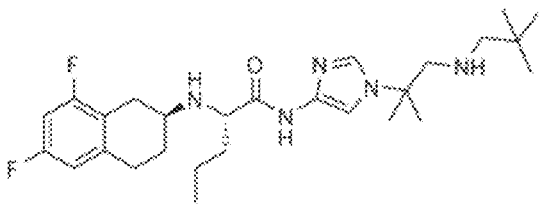
Figure 10C:
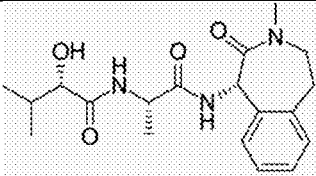
Figure 10C:
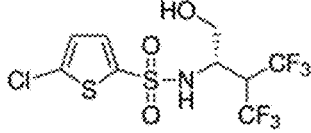
Figure 10C:
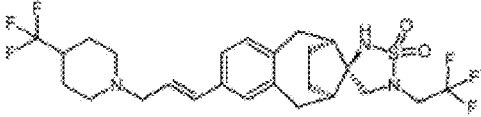
Figure 10C:
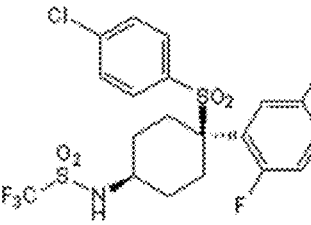
Figure 10C:
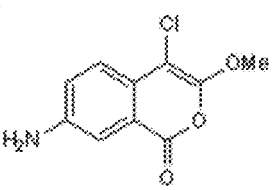
Figure 10C:
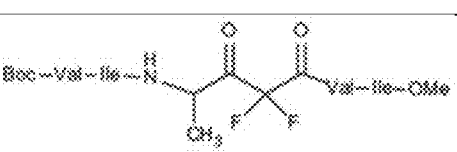
Figure 11A:
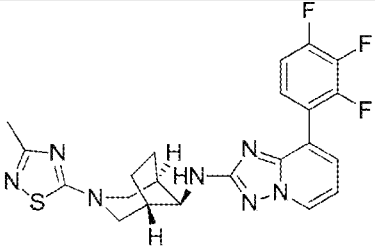
FIGS. 11A and 11B show structures of examples of GSMs including NGP555 and PF-06648671.
Figure 11A:
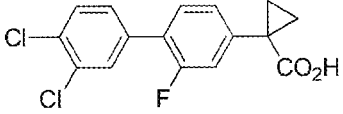
Figure 11A:
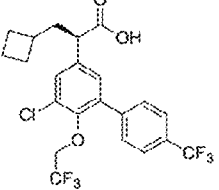
Figure 11A:
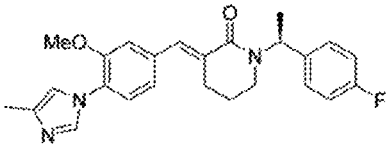
Figure 11A:
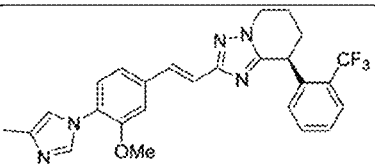
Figure 11A:
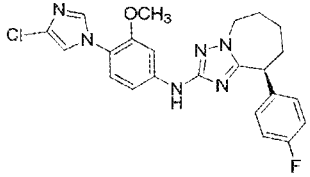
Figure 11A:
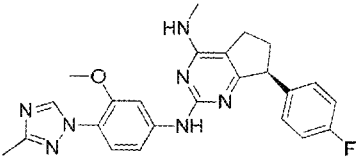
Figure 11B:
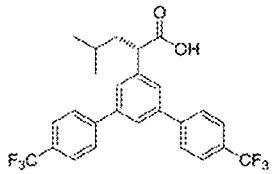
Figure 11B:
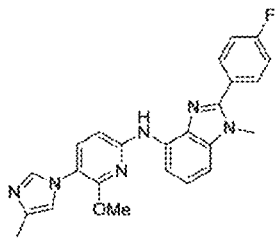
Figure 11B:
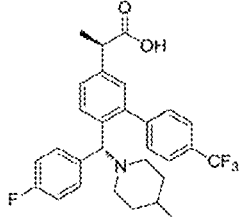
Figure 11B:
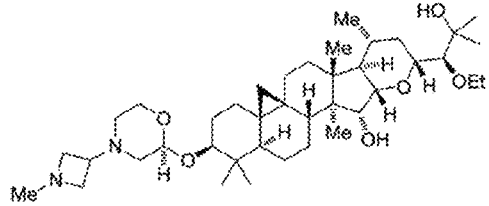
Figure 11B:
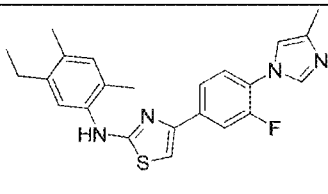
Figure 11B:
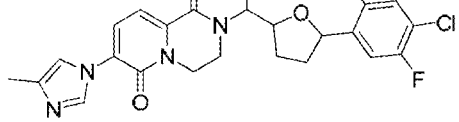
Figure 11B:
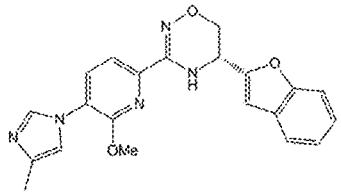

Beginning on day 0, male Hartley guinea pigs (450-500 g) were deafened by intraperitoneal administration of kanamycin (400 mg/kg) dosed once daily for 10 consecutive days. These conditions have been demonstrated to result in progressive loss of outer hair cells and a corresponding worsening of ABR thresholds which occurs in a base to apex gradient. A loss of synapse density in this model has not been described previously. On day 15, animals received bilateral transtympanic injections of vehicle (30 μl), crystalline Compound I (30 μl of 2% in vehicle), or crystalline Compound II (30 μl of 2% in vehicle). Three months after administration of test article, animals were euthanized and cochleae collected and stained with phalloidin and antibodies against CtBP2 and NF-200. The number of CtBP2+/NF-200+ synapses were quantified and normalized to the number of inner hair cells to obtain synapse density. Synapse density was decreased with kanamycin treatment at 14.7 and 17.3 mm from the apex of the cochlea, which in the guinea pig cochlea, tonally correlates with 16 and 32 kHz, respectively, according to the Greenwood frequency map. Synapse density was increased with gamma secretase treatment as shown in FIG. 9. These data are the first evidence of a restoration of synapse density with a gamma secretase inhibitor and suggest that this treatment paradigm could be beneficial for the treatment of synaptopathy.

Vehicle (PF10) and GSI in vehicle used in Examples 6 and 7 were prepared as follows: To 129 mL sterile water was added, 0.96 g sodium chloride, 0.59 g sodium phosphate dibasic, and 0.14 g sodium phosphate monobasic. The solution was stirred at ambient temperature and 25.6 g poloxamer 407 was added and stirred overnight to yield a clear solution. The solution was sterile filtered and 1 mL of the solution described above was added to 20 mg of crystalline Compound I or 20 mg of crystalline Compound II, and the suspension was vortexed for 60 minutes to yield a homogeneous suspension. Crystalline Compound I, crystalline Compound II and their preparation are described in U.S. Provisional Application 62/248,625 filed Oct. 30, 2015 and PCT Application PCT/US16/59194 filed Oct. 27, 2016, now WO2017075264, published May 4, 2017, each of which is hereby incorporated by reference.

In another embodiment, any one of the above described embodiments can be used alone or in combination with any one or more of the above described embodiments.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method for treating cochlear synaptopathy in a patient in need thereof comprising:
    administering to said patient a therapeutically effective amount of a compound selected from the group consisting of (2,2,3,3,3-pentafluoropropyl)-carbamic acid (S)-1-((S)-6-oxo-6,7-dihydro-5H-dibenzo [b,d]azepin-7-ylcarbamoyl) ethyl ester, (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl) malonamide,

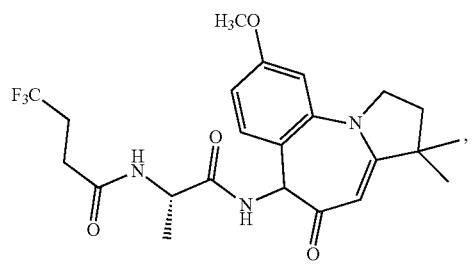

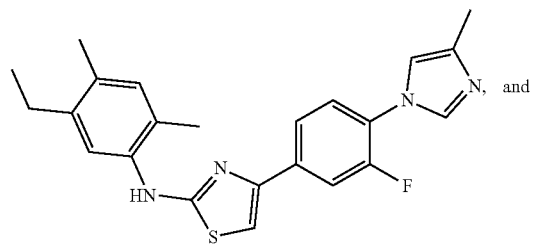

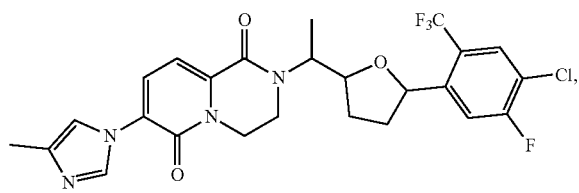

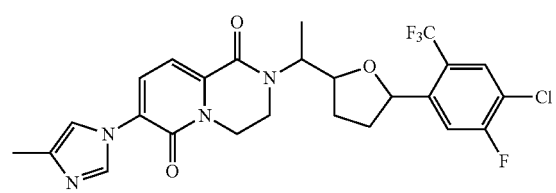 [SMILES: Cc1cn(-c2ccc3n(c2=O)CCN(C(C)C2CCC(c4cc(F)c(Cl)cc4C(F)(F)F)O2)C3=O)cn1]

or a pharmaceutically acceptable salt of any of the foregoing.

2. The method of claim 1, comprising administering

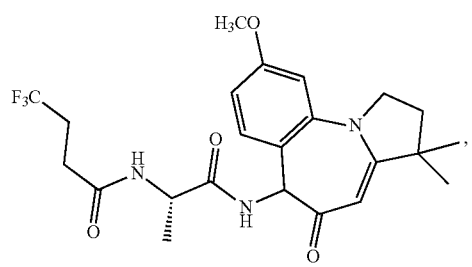 [SMILES: COc1ccc2c(c1)N1CCC(C)(C)C1=CC(=O)C2NC(=O)[C@H](C)NC(=O)CCC(F)(F)F]

or a pharmaceutically acceptable salt thereof.

3. The method of claim 1, comprising administering

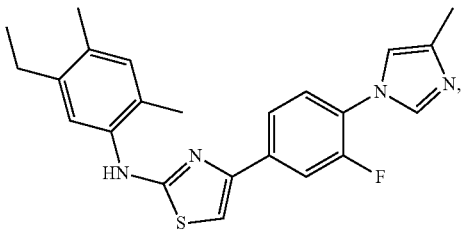 [SMILES: CCc1cc(Nc2nc(-c3ccc(-n4cnc(C)c4)c(F)c3)cs2)c(C)cc1C]

or a pharmaceutically acceptable salt thereof.

4. The method of claim 1, comprising administering

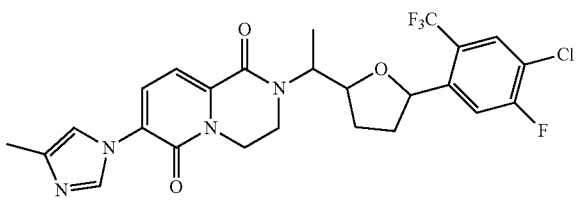 [SMILES: Cc1cn(-c2ccc3n(c2=O)CCN(C(C)C2CCC(c4cc(F)c(Cl)cc4C(F)(F)F)O2)C3=O)cn1]

or a pharmaceutically acceptable salt thereof.

5. The method of claim 1, comprising administering (2,2,3,3,3-pentafluoropropyl)-carbamic acid (S)-1-(S)-6-oxo-6,7-dihydro-5H-dibenzo[b,d]azepin-7-ylcarbamoyl) ethyl ester or a pharmaceutically acceptable salt thereof.

6. The method of claim 1, comprising administering (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, or a pharmaceutically acceptable salt thereof.

7. The method of claim 1, wherein said compound, or a pharmaceutically acceptable salt thereof, is administered to or near the round window of the cochlea.

8. The method of claim 1, wherein said compound, or a pharmaceutically acceptable salt thereof, is administered via the oral route.

9. The method of claim 1, wherein said compound or a pharmaceutically acceptable salt thereof, is administered intratympanically.

10. The method of claim 7, comprising administering

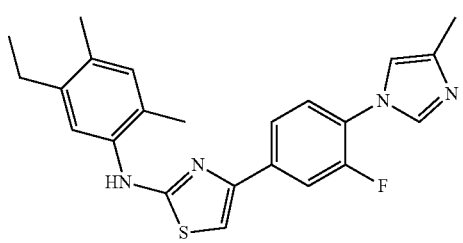 [SMILES: CCc1cc(Nc2nc(-c3ccc(-n4cnc(C)c4)c(F)c3)cs2)c(C)cc1C]

or a pharmaceutically acceptable salt thereof.

11. The method of claim 7, comprising administering

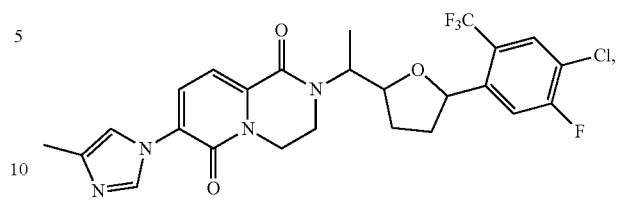

or a pharmaceutically acceptable salt thereof.

12. The method of claim 7, comprising administering (2,2,3,3,3-pentafluoropropyl)-carbamic acid (S)-1-((S)-6-oxo-6,7-dihydro-5H-dibenzo [b,d]azepin-7-ylcarbamoyl) ethyl ester or a pharmaceutically acceptable salt thereof.

13. The method of claim 7, comprising administering (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, or a pharmaceutically acceptable salt thereof.

14. The method of claim 8, comprising administering

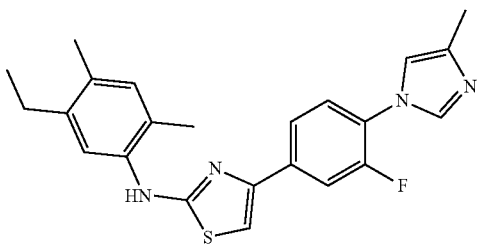 [SMILES: CCc1cc(Nc2nc(-c3ccc(-n4cnc(C)c4)c(F)c3)cs2)c(C)cc1C]

or a pharmaceutically acceptable salt thereof.

15. The method of claim 8, comprising administering

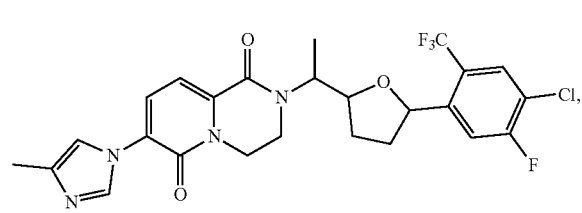 [SMILES: Cc1cn(-c2ccc3n(c2=O)CCN(C(C)C2CCC(c4cc(F)c(Cl)cc4C(F)(F)F)O2)C3=O)cn1]

or a pharmaceutically acceptable salt thereof.

16. The method of claim 8, comprising administering (2,2,3,3,3-pentafluoropropyl)-carbamic acid (S)-1-((S)-6-oxo-6,7-dihydro-5H-dibenzo [b,d]azepin-7-ylcarbamoyl) ethyl ester or a pharmaceutically acceptable salt thereof.

17. The method of claim 8, comprising administering (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, or a pharmaceutically acceptable salt thereof.

18. The method of claim 9, comprising administering

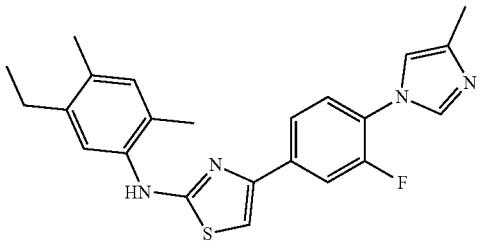 [SMILES: CCc1cc(Nc2nc(-c3ccc(-n4cnc(C)c4)c(F)c3)cs2)c(C)cc1C]

or a pharmaceutically acceptable salt thereof.

19. The method of claim 9 comprising administering

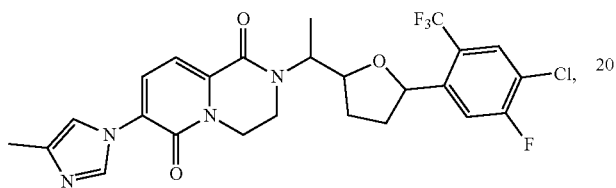

or a pharmaceutically acceptable salt thereof.

20. The method of claim 9, comprising administering (2,2,3,3,3-pentafluoropropyl)-carbamic acid (S)-1-((S)-6-oxo-6,7-dihydro-5H-dibenzo [b,d]azepin-7-ylcarbamoyl) ethyl ester, or a pharmaceutically acceptable salt thereof.

21. The method of claim 9, comprising administering (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, or a pharmaceutically acceptable salt thereof.

22. The method of claim 1, wherein said compound, or a pharmaceutically acceptable salt thereof, is administered in a pharmaceutical composition comprising a pharmaceutically acceptable aqueous solution comprising:
   (A) approximately 15% to 25% by weight (w/w) of poloxamer 407; or
   (B) (i) approximately 15% to 25% by weight (w/w) of poloxamer 407 and
      (ii) approximately 0.5% to 4% by weight (w/w) of hydroxypropyl methylcellulose having a nominal viscosity of 40-60 cP or grade 80-120 cP; or
   (C) (i) approximately 10%-20% by weight (w/w) of poloxamer 407, and
      (ii) approximately 0.1%-0.3% by weight (w/w) of Carbopol® 974P; or
   (D) (i) approximately 0.5% to 8% by weight (w/w) of a hyaluronic acid; or
   (E) (i) approximately 0.5% to 4% by weight (w/w) of a hyaluronic acid, and
      (ii) approximately 5% to 20% by volume of polyethylene glycol 400;
   wherein said compound is present in approximately 0.01% to about 20% w/v of said aqueous solution.

23. The method of claim 22 wherein said compound is selected from the group consisting of crystalline (2,2,3,3,3-pentafluoropropyl)-carbamic acid (S)-1-((S)-6-oxo-6,7-dihydro-5H-dibenzo [b,d]azepin-7-ylcarbamoyl) ethyl ester and crystalline (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, or a pharmaceutically acceptable salt thereof.

24. The method of claim 22, wherein said pharmaceutically acceptable aqueous solution comprises approximately 15% to 25% by weight (w/w) of poloxamer 407.

25. The method of claim 22, wherein said pharmaceutically acceptable aqueous solution comprises approximately 15% to 25% by weight (w/w) of poloxamer 407, and wherein said compound is present in approximately 0.1% to 5% w/v, and is selected from the group consisting of crystalline (2,2,3,3,3-pentafluoropropyl)-carbamic acid (S)-1-((S)-6-oxo-6,7-dihydro-5 H-dibenzo [b,d]azepin-7-ylcarbamoyl) ethyl ester and crystalline (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide, or a pharmaceutically acceptable salt of any of the foregoing.

26. The method of claim 7, comprising administering

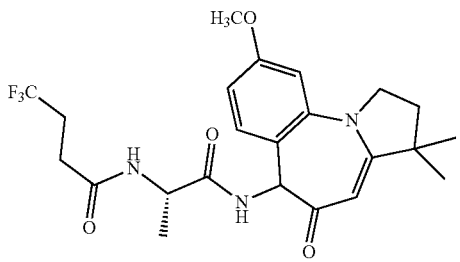 [SMILES: COc1ccc2c(c1)N1CCC(C)(C)C1=CC(=O)C2NC(=O)[C@H](C)NC(=O)CCC(F)(F)F]

or a pharmaceutically acceptable salt thereof.

27. The method of claim 8, comprising administering

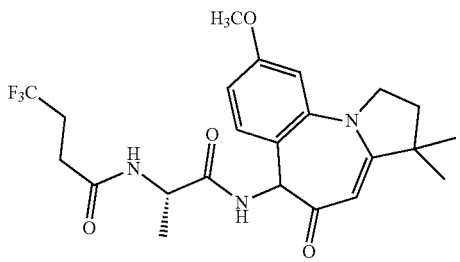 [SMILES: COc1ccc2c(c1)N1CCC(C)(C)C1=CC(=O)C2NC(=O)[C@H](C)NC(=O)CCC(F)(F)F]

or a pharmaceutically acceptable salt thereof.

28. The method of claim 9, comprising administering

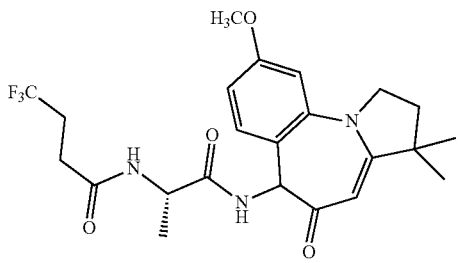 [SMILES: COc1ccc2c(c1)N1CCC(C)(C)C1=CC(=O)C2NC(=O)[C@H](C)NC(=O)CCC(F)(F)F]

or a pharmaceutically acceptable salt thereof.

* * * * *